US011559316B2

(12) United States Patent
Dacosta et al.

(10) Patent No.: US 11,559,316 B2
(45) Date of Patent: Jan. 24, 2023

(54) BONE FIXATION SYSTEM, ASSEMBLY, IMPLANTS, DEVICES, INSERTION GUIDES, AND METHODS OF USE

(71) Applicant: Paragon 28, Inc., Englewood, CO (US)

(72) Inventors: Albert Dacosta, Lone Tree, CO (US); Byron L. Hutchinson, Seattle, WA (US); Spanky Raymond, Uniontown, OH (US); Daniel J. Lee, Denver, CO (US); Francis D. Barmes, Parker, CO (US); Laura Zagrocki Brinker, Lone Tree, CO (US)

(73) Assignee: Paragon 28, Inc., Englewood, CO (US)

( * ) Notice: Subject to any disclaimer, the term of this patent is extended or adjusted under 35 U.S.C. 154(b) by 276 days.

(21) Appl. No.: 17/068,086

(22) Filed: Oct. 12, 2020

(65) Prior Publication Data

US 2021/0022781 A1 Jan. 28, 2021

Related U.S. Application Data

(60) Division of application No. 16/035,333, filed on Jul. 13, 2018, now Pat. No. 10,799,276, which is a
(Continued)

(51) Int. Cl.
*A61B 17/80* (2006.01)
*A61B 17/17* (2006.01)
(Continued)

(52) U.S. Cl.
CPC ...... *A61B 17/1775* (2016.11); *A61B 17/1682* (2013.01); *A61B 17/1728* (2013.01);
(Continued)

(58) Field of Classification Search
CPC .......................... A61B 17/1775; A61B 17/808
See application file for complete search history.

(56) References Cited

U.S. PATENT DOCUMENTS

| 5,350,380 A | 9/1994 | Goble |
| 5,352,228 A | 10/1994 | Kummer |

(Continued)

FOREIGN PATENT DOCUMENTS

| EP | 0617927 | 10/1994 |
| EP | 1273271 | 8/2007 |

(Continued)

OTHER PUBLICATIONS

Partial Supplementary European Search Report issued in European Patent Application No. 18777784.2, dated Jan. 14, 2021, 13 pages.
(Continued)

*Primary Examiner* — Christian A Sevilla
(74) *Attorney, Agent, or Firm* — Heslin Rothenberg Farley & Mesiti P.C.; Jacquelyn A. Graff, Esq.

(57) ABSTRACT

Guides, implants, devices, instruments, systems, and assemblies for achieving bone fusion are disclosed. A bone fusion system, including an implant template, a guide wire for insertion through the implant template, a bone plate for receiving the guide wire, and an alignment guide apparatus for coupling to the bone plate. Methods of using a bone fusion system for achieving bone fusion are also disclosed.

20 Claims, 25 Drawing Sheets

Related U.S. Application Data continuation of application No. PCT/US2018/041657, filed on Jul. 11, 2018.

(60) Provisional application No. 62/530,909, filed on Jul. 11, 2017.

(51) Int. Cl.
    *A61B 17/16* (2006.01)
    *A61B 17/56* (2006.01)

(52) U.S. Cl.
    CPC ........ *A61B 17/808* (2013.01); *A61B 17/8057* (2013.01); *A61B 17/8061* (2013.01); *A61B 2017/564* (2013.01)

(56) References Cited

U.S. PATENT DOCUMENTS

| | | | |
|---|---|---|---|
| 5,429,641 | A | 7/1995 | Gotfried |
| 5,458,602 | A | 10/1995 | Goble |
| 6,342,057 | B1 | 1/2002 | Brace |
| 6,692,496 | B1 | 2/2004 | Wardlaw |
| 7,011,665 | B2 | 3/2006 | Null |
| 7,316,687 | B2 | 1/2008 | Aikins |
| 7,785,326 | B2 | 8/2010 | Green |
| 7,819,877 | B2 | 10/2010 | Guzman |
| 8,206,389 | B2 | 6/2012 | Huebner |
| 8,231,627 | B2 | 7/2012 | Huebner |
| 8,535,355 | B2 | 9/2013 | Prasad |
| 8,821,508 | B2 * | 9/2014 | Medoff ............. A61B 17/8061 606/99 |
| 9,044,250 | B2 | 6/2015 | Olsen et al. |
| 9,119,721 | B2 * | 9/2015 | Sharkey ................... A61F 2/38 |
| 9,161,796 | B2 | 10/2015 | Chiodo |
| 9,241,744 | B2 | 1/2016 | Blake |
| 9,421,103 | B2 | 8/2016 | Jeng et al. |
| 2004/0102776 | A1 | 5/2004 | Huebner |
| 2004/0102777 | A1 | 5/2004 | Huebner |
| 2004/0193165 | A1 | 9/2004 | Orbay |
| 2005/0033301 | A1 | 2/2005 | Lombardo |
| 2006/0189996 | A1 | 8/2006 | Orbay |
| 2006/0264944 | A1 * | 11/2006 | Cole ..................... A61B 17/725 606/62 |
| 2007/0173843 | A1 | 7/2007 | Matityahu |
| 2007/0225714 | A1 | 9/2007 | Gradl |
| 2007/0239168 | A1 | 10/2007 | Keunzi |
| 2007/0265634 | A1 | 11/2007 | Weinstein |
| 2007/0270850 | A1 | 11/2007 | Geissler |
| 2008/0015590 | A1 | 1/2008 | Sanders |
| 2008/0188852 | A1 | 8/2008 | Matityahu |
| 2009/0036931 | A1 | 2/2009 | Pech |
| 2009/0088767 | A1 | 4/2009 | Leyden |
| 2009/0093849 | A1 | 4/2009 | Grabowski |
| 2009/0157086 | A1 * | 6/2009 | Digeser ............. A61B 17/1728 606/280 |
| 2010/0087824 | A1 | 4/2010 | Collazo |
| 2010/0121324 | A1 | 5/2010 | Tyber |
| 2010/0179597 | A1 | 7/2010 | Henderson |
| 2011/0046681 | A1 | 2/2011 | Prandi et al. |
| 2011/0093018 | A1 * | 4/2011 | Prasad ................ A61B 17/8014 606/282 |
| 2011/0144647 | A1 | 6/2011 | Appenzeller et al. |
| 2011/0218576 | A1 | 9/2011 | Galm |
| 2011/0224734 | A1 | 9/2011 | Schelling |
| 2011/0264149 | A1 | 10/2011 | Pappalardo |
| 2011/0270319 | A1 * | 11/2011 | Sheffer ............. A61B 17/1728 606/280 |
| 2011/0282397 | A1 | 11/2011 | Richter |
| 2012/0078252 | A1 | 3/2012 | Huebner |
| 2012/0303038 | A1 | 11/2012 | Durante |
| 2012/0316562 | A1 | 12/2012 | Costa |
| 2013/0046311 | A1 | 2/2013 | Blake et al. |
| 2013/0150903 | A1 | 6/2013 | Vincent |
| 2013/0172942 | A1 * | 7/2013 | Lewis ................ A61B 17/8061 606/281 |
| 2014/0066996 | A1 | 3/2014 | Price et al. |
| 2014/0107798 | A1 | 4/2014 | Jeng et al. |
| 2014/0180348 | A1 | 6/2014 | Thoren et al. |
| 2015/0032168 | A1 | 1/2015 | Orsak et al. |
| 2015/0150683 | A1 | 6/2015 | Donner et al. |
| 2015/0182267 | A1 | 7/2015 | Wolf et al. |
| 2015/0245923 | A1 | 9/2015 | Abdou |
| 2015/0359580 | A1 * | 12/2015 | Dacosta ............. A61B 17/8897 606/281 |
| 2016/0030064 | A1 | 2/2016 | Dacosta et al. |
| 2016/0135858 | A1 | 5/2016 | Dacosta et al. |
| 2016/0235414 | A1 | 8/2016 | Hatch et al. |
| 2016/0242791 | A1 | 8/2016 | Fallin et al. |
| 2016/0310191 | A1 | 10/2016 | Seykora et al. |
| 2017/0056031 | A1 | 3/2017 | Awtrey et al. |
| 2017/0216043 | A1 | 8/2017 | Surma et al. |
| 2018/0110530 | A1 | 4/2018 | Wagner et al. |

FOREIGN PATENT DOCUMENTS

| | | |
|---|---|---|
| EP | 2745786 | 6/2014 |
| EP | 3023068 | 5/2016 |
| FR | 3030221 | 6/2016 |
| JP | 04250156 | 9/1992 |
| WO | 9415556 | 7/1994 |
| WO | 2005089660 | 9/2005 |
| WO | 2009052294 | 4/2009 |
| WO | 2012103335 | 8/2012 |
| WO | 2012106477 | 8/2012 |
| WO | 2013009574 | 1/2013 |
| WO | 2014105750 | 7/2014 |
| WO | 2015094409 | 6/2015 |
| WO | 2015138542 | 9/2015 |
| WO | 2017004221 | 1/2017 |
| WO | 2017011656 | 1/2017 |
| WO | 2018081185 | 5/2018 |
| WO | 2018157170 | 8/2018 |

OTHER PUBLICATIONS

Extended European Search Report issued in European Patent Application No. 18757770.5, dated Mar. 9, 2021, 10 pages.
Extended European Search Report issued in European Patent Application No. 18758239.0, dated Apr. 8, 2021, 12 pages.
Extended European Search Report issued in European Patent Application No. 18831633.5, dated Apr. 16, 2021, 10 pages.
Extended European Search Report issued in European Patent Application No. 18777784.2, dated Apr. 16, 2021, 11 pages.
Paragon 28, Inc., "Intramedullary Nail Alignment Guides, Fixation Guides, Devices, Systems, and Methods of Use," International Application No. PCT/US2018/020046, Feb. 27, 2018, 78 pages.
Paragon 28, Inc., "Targeting Instruments, Systems and Methods of Use," International Application No. PCT/US2018/020053, Feb. 27, 2018, 56 pages.
Paragon 28, Inc., "Intramedullary Nail Alignment Guides, Fixation Guides, Devices, Systems, and Methods of Use," U.S. Appl. No. 15/907,850, filed Feb. 28, 2018, 60 pages.
Paragon 28, Inc., "Targeting Instruments, Systems and Methods of Use," U.S. Appl. No. 15/908,048, filed Feb. 28, 2018, 51 pages.
Paragon 28, Inc., "Bone Fixation System, Assembly, Implants, Devices, Alignment Guides, and Methods of Use," U.S. Appl. No. 15/942,040, filed Mar. 30, 2018, 61 pages.
Paragon 28, Inc., "Bone Fixation System, Assembly, Implants, Devices, Alignment Guides, and Methods of Use," International Application No. PCT/US2018/025443, Mar. 30, 2018, 66 pages.
Paragon 28, Inc., "Bone Fixation System, Assembly, Implants, Devices, Insertion Guides, and Methods of Use," International Application No. PCT/US2018/041657, Jul. 11, 2018, 57 pages.
International Search Report and Written Opinion of the International Searching Authority for PCT/US2018/025443, dated Aug. 1, 2018, 12 pages.
Budny et al. "Naviculocuneiform Arthrodesis," Clinics in Podiatric Medicine and Surgery, vol. 24, pp. 753-763, Oct. 2007.
Kamat et al. "Laparoscopic extraction of fractured Kirschner wire from the pelvis," Journal of Minimal Access Surgery, vol. 10, No. 2, pp. 97-98, Jun. 2014.

(56) References Cited

OTHER PUBLICATIONS

International Search Report and Written Opinion of the International Searching Authority for PCT/US2018/041657, dated Nov. 14, 2018, 21 pages.
Partial Supplementary European Search Report issued in European Patent Application No. 18757770.5 dated Dec. 3, 2020, 11 pages.
Partial Supplementary European Search Report issued in European Patent Application No. 18758239.0, dated Dec. 10, 2020, 11 pages.
European Communication Pursuant to Article 94(3) EPC (Office Action) for EP Application No. 18201132.0 dated Feb. 12, 2021, 5 pages.
Extended European Search Report (EESR) for EP Application No. 17863986.0, dated Sep. 15, 2020 (13 pages).

* cited by examiner

BONE FIXATION SYSTEM, ASSEMBLY, IMPLANTS, DEVICES, INSERTION GUIDES, AND METHODS OF USE

CROSS REFERENCE TO RELATED APPLICATIONS

This application is a divisional of U.S. application Ser. No. 16/035,333 filed Jul. 13, 2018, which is a continuation of PCT Application No. PCT/US2018/041657 filed on Jul. 11, 2018, which claims priority benefit under 35 U.S.C. § 119(e) of U.S. provisional application No. 62/530,909, filed Jul. 11, 2017, which is incorporated herein by reference in its entirety.

TECHNICAL FIELD

The present invention relates generally to general, podiatric, and orthopaedic surgery related to fixation of fractured bones. More specifically, but not exclusively, the present invention relates to guides, implants, devices, instruments, systems, assemblies and methods for achieving bone fusion.

BACKGROUND OF THE INVENTION

There are generally two currently available solutions for fusing the navicular-cuneiform joint when a patient has navicular-cuneiform joint arthritis or a flatfoot deformity. The first solution involves using multiple interfrag screws to fuse the medial cuneiform-navicular and/or intermediate cuneiform-navicular. The interfrag screw assembly is able to compress multiple joints, including the cuneiform-navicular joint. The interfrag screw assembly may include three interfrag screws and a surgeon's precision and expertise to properly place the screws to avoid interfering with one another. However, the interfrag screw assembly may require an additional plantar incision and interfrag screw to resist plantar gapping. Interfrag screw assemblies are generally less rigid than plate systems.

The second solution involves using at least one plate that straddles the navicular-cuneiform joint and which is attached with bone screws. The plating technique provides a stronger construct than the interfrag screws. However, the currently available plating techniques are limited to being used for fusing and/or compressing the navicular-cuneiform joint, typically, the medial cuneiform-navicular joint. Additionally, if an interfrag screw is used in combination with a plate, there is often difficulty with screw interference when attempting to place several screws in a relatively small area. Thus, new and improved bone fixation systems, guides, implants, devices, instruments, systems, assemblies and methods for achieving bone fusion are needed to overcome the above-noted drawbacks of the currently available solutions for fusing the navicular-cuneiform joint.

SUMMARY OF THE INVENTION

The present invention is directed toward devices and methods for use in fusing bones. The guides, implants, devices, instruments, systems, assemblies and methods for achieving bone fusion, may be used for fusing the navicular-cuneiform joints.

In one aspect of the present invention provided herein, is a bone fusion system. The bone fusion system including an implant template, a guide wire for insertion through the implant template, an implant for receiving the guide wire, and an alignment guide apparatus for coupling to the implant.

In another aspect of the present invention provided herein, is an implant template. The implant template including a first distal lobe positioned on a plantar side of a first end of the implant template. The implant template also includes a second distal lobe positioned on a dorsal side of the first end of the implant template. In addition, the implant template includes a proximal lobe positioned on the plantar side of a second end of the implant template. Finally, the implant template includes a proximal drill guide member positioned on the dorsal side of the second end of the implant template.

In yet another aspect of the present invention provided herein is an alignment guide apparatus. The alignment guide apparatus including a body with an arm having a first end and a second end, an attachment portion at the first end, and an alignment portion at the second end. The alignment guide apparatus further including a fixation member, wherein the fixation member extends through the attachment portion. The alignment guide apparatus also includes a guide pin protector, wherein the guide pin protector extends through the alignment portion. Finally, the alignment guide apparatus may include a compression screw configured to engage the guide pin protector.

In a further aspect of the present invention provided herein, is a plate. The plate including an angled lobe positioned on a dorsal side of a proximal end of the plate, wherein the angled lobe is angled relative to a horizontal plane and a top plane of the plate. The angled lobe includes a bone contacting surface, wherein the bone contacting surface is semi-circular. The plate may also include a first distal lobe positioned on a plantar side of a distal end of the plate, a second distal lobe positioned on the dorsal side of the distal end of the plate, and a proximal lobe positioned on a plantar side of the proximal end of the plate.

In yet another aspect of the present invention provided herein, is a method of using a bone fusion system for fusing bones. The method includes creating an incision over the navicular-cuneiform joint and preparing the joint for fusion. The method also includes coupling a template to the joint with at least one wire and using the template to form a recessed region in a navicular bone. Further, the method includes removing the template from the navicular-cuneiform joint and positioning a plate on the navicular-cuneiform joint. Finally, the method includes inserting bone screws through the plate to secure the plate to the navicular-cuneiform joint.

These and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION FOR CARRYING OUT THE INVENTION

Figure 1:
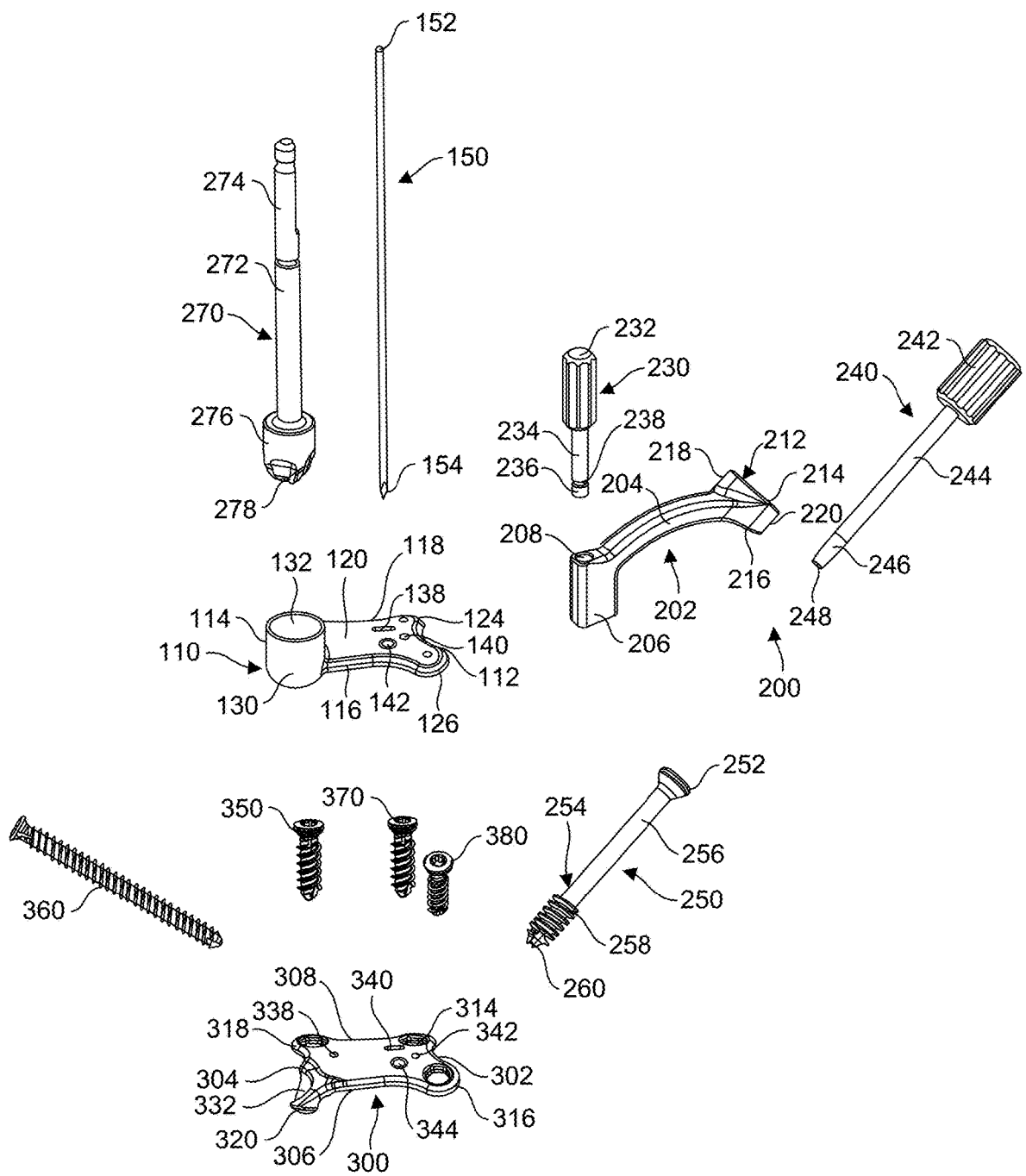
FIG. 1 is an exploded top perspective view of one embodiment of a bone fusion system, in accordance with an aspect of the present invention.

Generally stated, disclosed herein are guides, implants, devices, instruments, systems, and assemblies for achieving bone fusion. Further, methods for using the guides, implants, devices, instruments, systems, and assemblies to achieve bone fusion are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right foot may be mirrored so that they likewise function with the left foot. Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Figure 2:
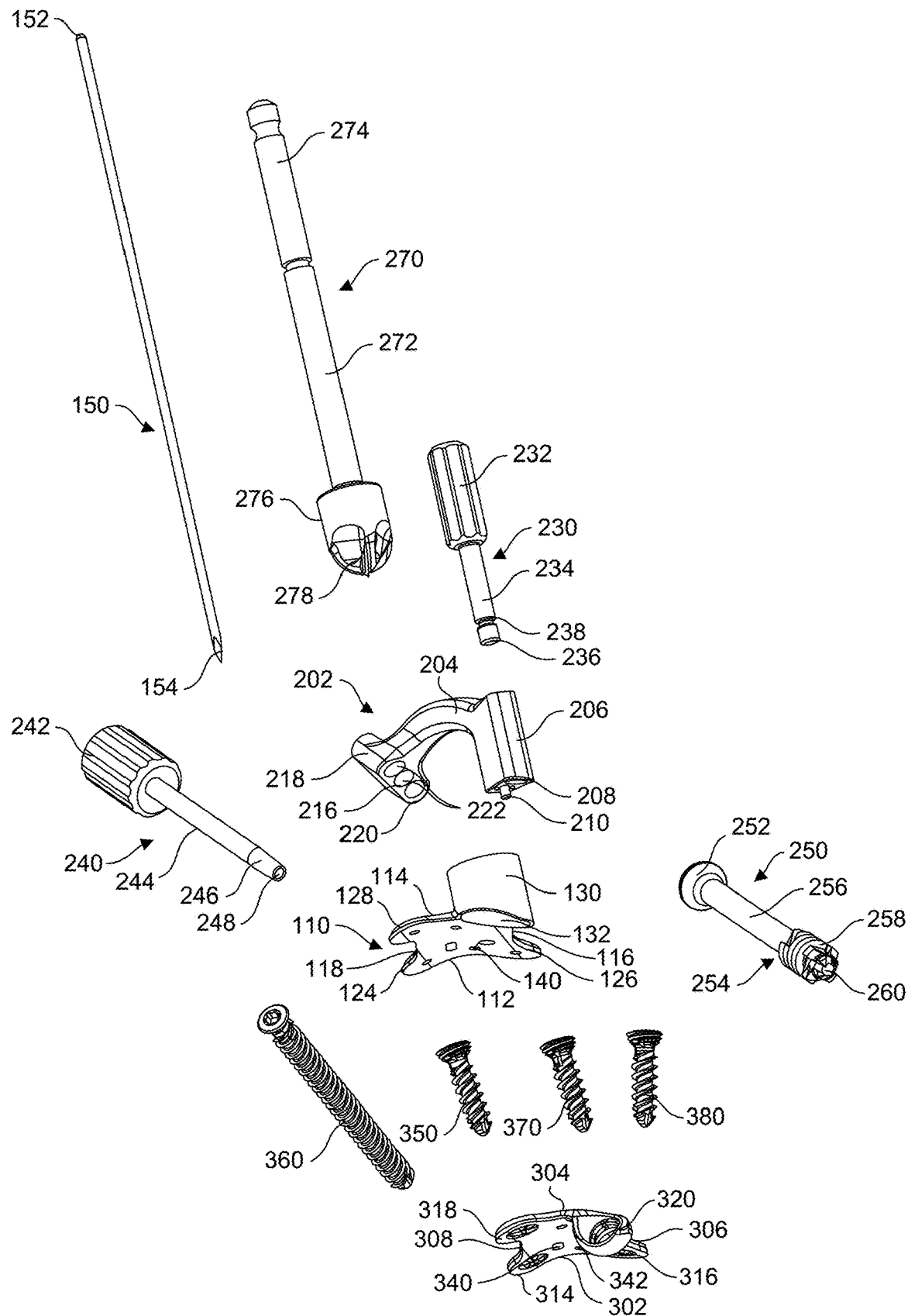
FIG. 2 is an exploded bottom perspective view of the bone fusion system of FIG. 1, in accordance with an aspect of the present invention.
Figure 3:
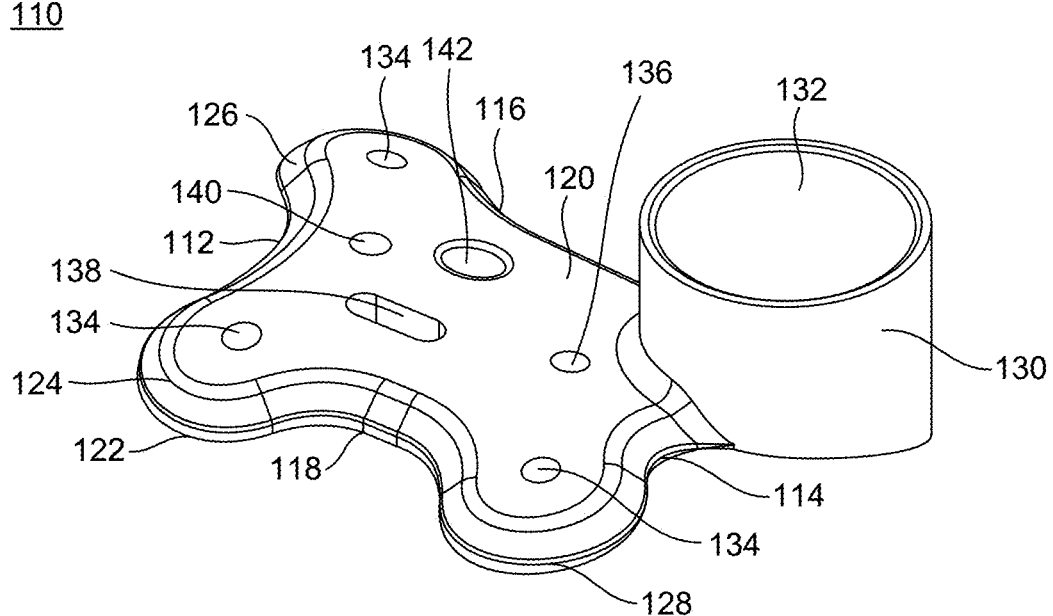
FIG. 3 is a first side perspective view of an implant template of the bone fusion system of FIG. 1, in accordance with an aspect of the present invention.
Figure 4:
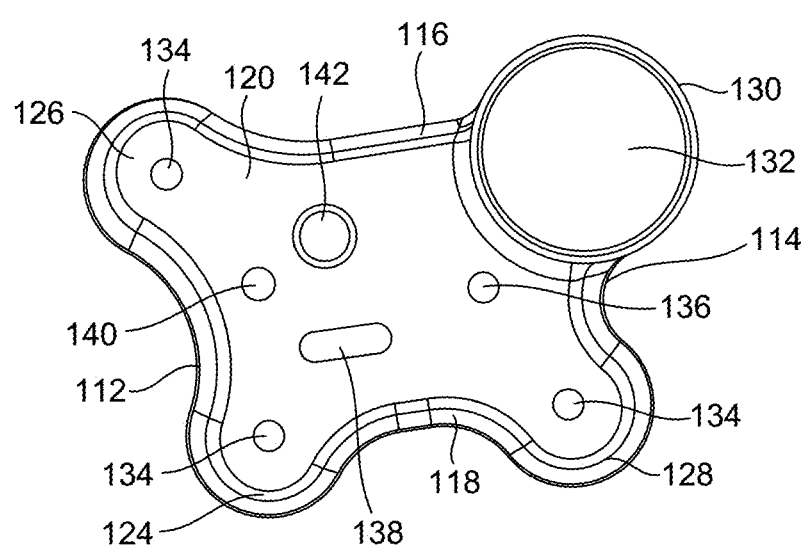
FIG. 4 is a first side view of the implant template of FIG. 3, in accordance with an aspect of the present invention.
Figure 5:
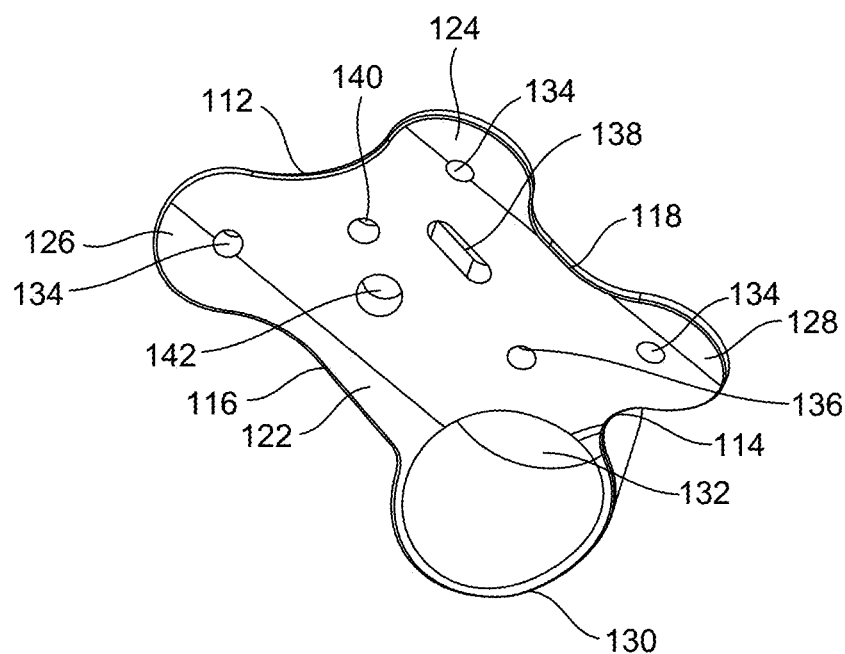
FIG. 5 is a second side perspective view of the implant template of FIG. 3, in accordance with an aspect of the present invention.
Figure 6:
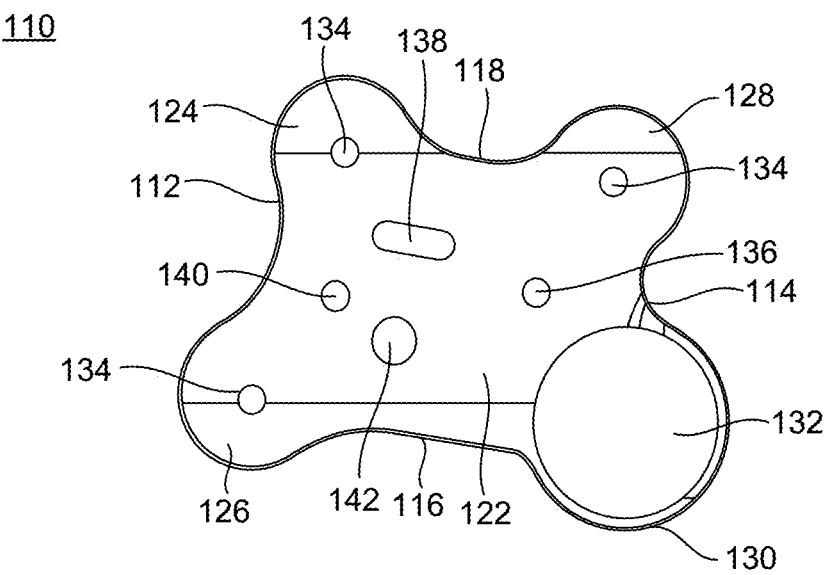
FIG. 6 is a second side view of the implant template of FIG. 3, in accordance with an aspect of the present invention.
Figure 7:
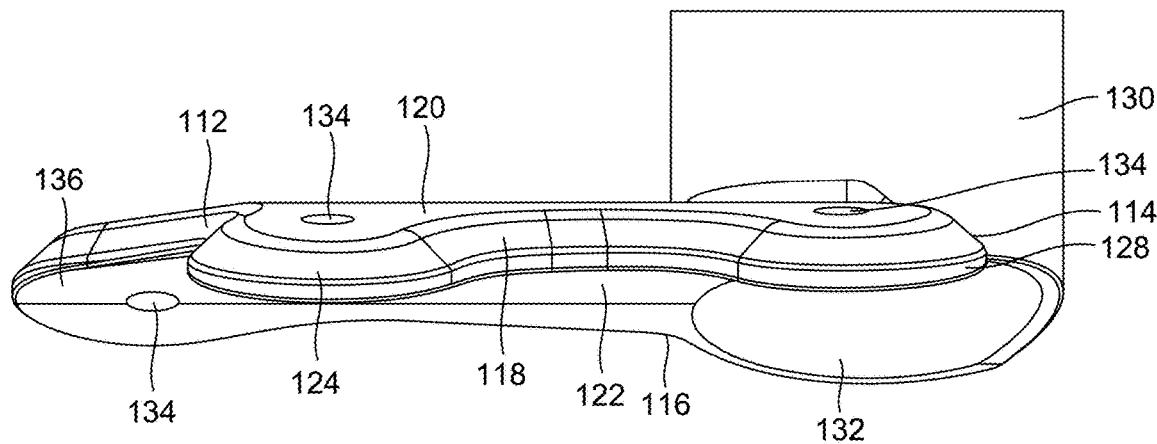
FIG. 7 is a plantar side view of the implant template of FIG. 3, in accordance with an aspect of the present invention.
Figure 8:
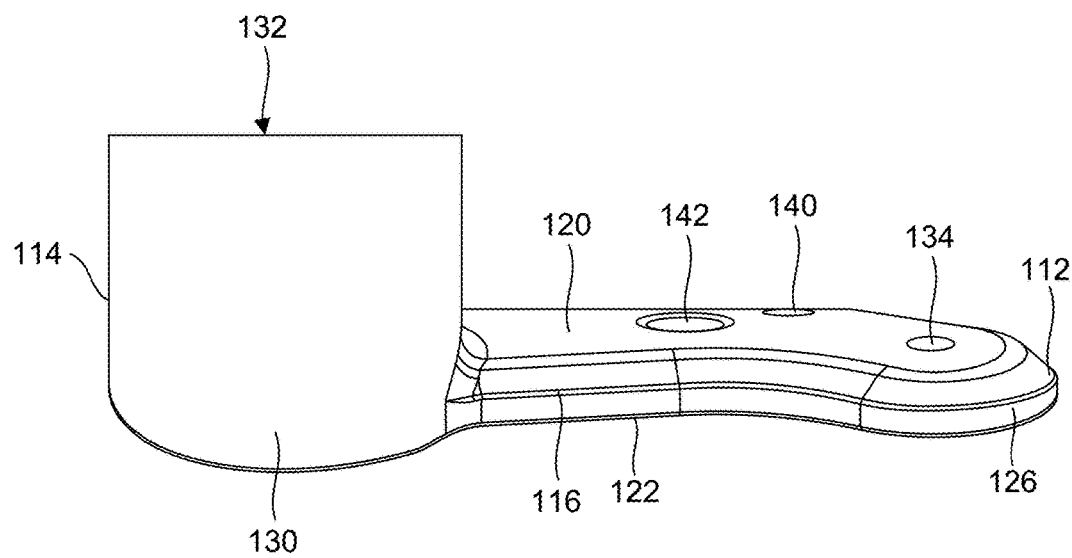
FIG. 8 is a dorsal side view of the implant template of FIG. 3, in accordance with an aspect of the present invention.

Referring to the drawings, wherein like reference numerals are used to indicate like or analogous components throughout the several views, and with particular reference to FIGS. 1 and 2, there is illustrated an exemplary embodiment of a bone fusion system 100. The bone fusion system 100 includes a plate or implant template 110, a guide wire 150, an alignment guide apparatus 200, a compression or lag fastener 250, a drill bit 270, a plate or implant 300, and bone screws 350, 360, 370, 380. The plate template 110, the guide wire 150, the alignment guide apparatus 200, and the drill bit 270 may be used to prepare a patient's bones for receiving the plate 300 and bone screws 350, 360, 370, 380, as described in greater detail below with reference to FIGS. 27-45. The compression fastener or lag screw 250 may be inserted, for example, after the plate is aligned on or secured to the patient's bones or while the patient's bones are being prepared for implantation of the plate 300, as described in greater detail below with reference to FIGS. 27-45.

Figure 9:
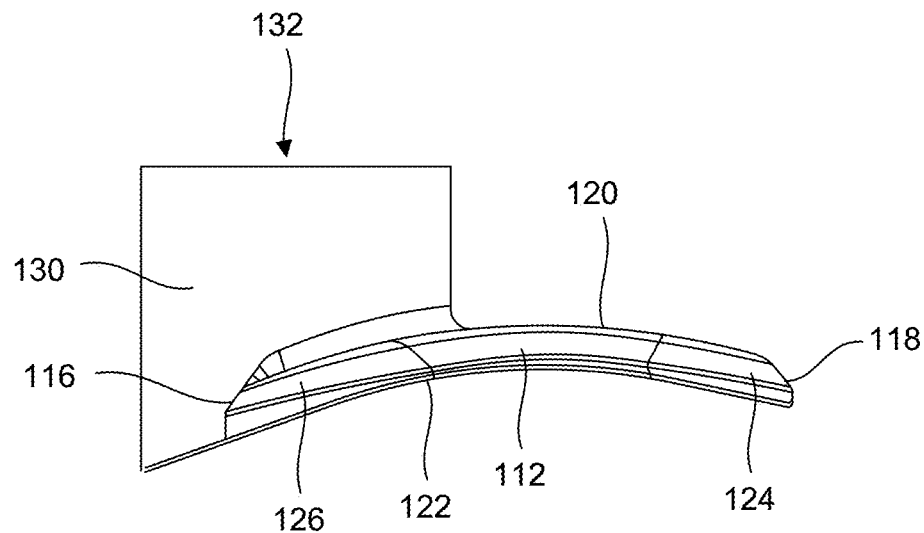
FIG. 9 is a distal end view of the implant template of FIG. 3, in accordance with an aspect of the present invention.
Figure 10:
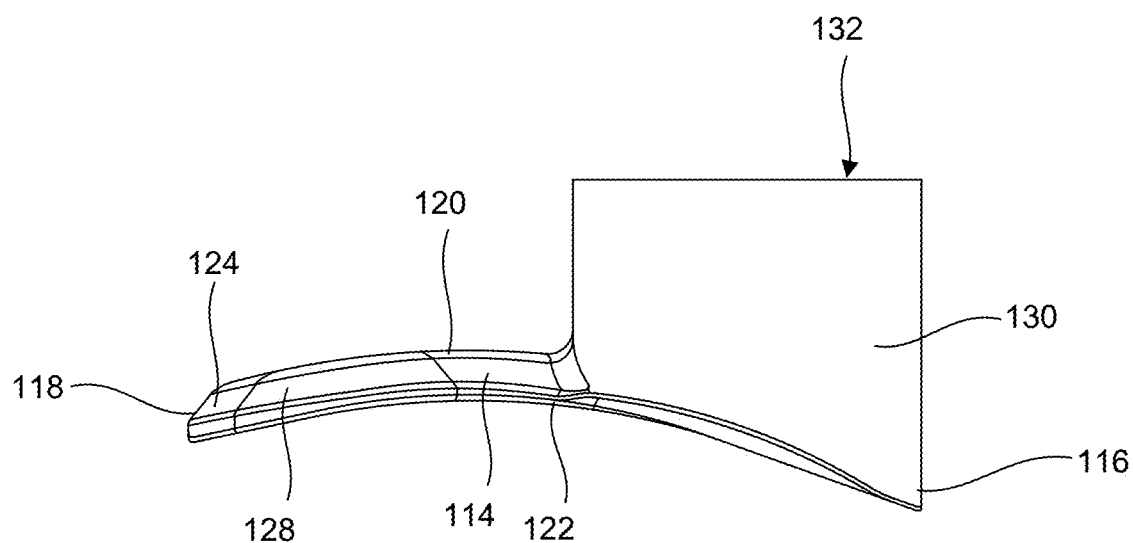
FIG. 10 is a proximal end view of the implant template of FIG. 3, in accordance with an aspect of the present invention.

Referring now to FIGS. 3-10, the template 110 is shown. The template 110 may include a first or distal end 112 opposite a second or proximal end 114, a top or dorsal side 116 opposite a bottom or plantar side 118, and a first side or exterior surface 120 opposite a second side, interior surface or bone facing surface 122. As shown in FIGS. 9 and 10, the template 110 may be, for example, curved as it extends between the dorsal side 116 and plantar side 118.

As shown in FIGS. 3-6, the template 110 may also include a first distal, plantar lobe, ear, or tab 124 extending away from the corner of the template 110 where the distal end 112 contacts the plantar side 118. The template 110 may further include a second distal, dorsal lobe, ear, or tab 126 extending away from the corner of the template 110 where the distal end 112 contacts the dorsal side 116, as shown in FIGS. 3-6. In addition, the template 110 may include a proximal, plantar lobe, ear, or tab 128 extending away from the corner of the template 110 where the proximal end 114 contacts the plantar side 118, as shown in FIGS. 3-6. Further, the template 110 may include a proximal, dorsal drill guide member or drill guide portion 130 positioned where the proximal end 114 contacts the dorsal side 116, as shown in FIGS. 3-6. The drill guide member 130 may extend from the second side 122 of the template 110 and out past the first side 120 of the template 110 forming a protrusion extending away from the proximal, dorsal portion of the template 110. Alternatively, the drill guide member 130 may extend out past the second side 122 of the template 110 to the first side 120 or extend out past the first side 120 of the template 110. The drill guide member 130 may include a drill opening or through hole 132. The drill opening 132 may be, for example, sized and shaped or configured to receiving a drill bit, such as, drill bit 270 as shown in FIGS. 1 and 2. The drill bit 270 may be, for example, sized and shaped to allow for a hole to be prepared, for example, reamed, that is sized and shaped to receive the second proximal lobe 320 of the plate 300. The template 110 may also include a plurality of fastener guide openings 134. A fastener guide opening 134 may be positioned in each of the distal, plantar lobe 124, the distal, dorsal lobe 126, and the proximal, plantar lobe 128, as shown in FIGS. 3-6. The fastener guide openings 134 may be, for example, sized and shaped to receive a guide wire, k-wire, olive-wire, alignment wire, pin or the like to assist with positioning the template 110 onto the patient's bones.

With continued reference to FIGS. 3-10, the template 110 may include an alignment opening 136 and a positioning slot 138 for receiving guide wires, k-wires, olive wires, pins, or alignment wires 150. The alignment opening 136 may be positioned, for example, near the proximal end 114 of the template and near a mid-point between the dorsal side 116 and plantar side 118 of the template 110. The alignment opening 136 may extend through the template 110 from the exterior surface 120 to the interior surface 122. The positioning slot 138 may be positioned, for example, between a mid-point along the longitudinal axis of the template 110 and the distal end 112. The positioning slot 138 may have, for example, a length and a width and the length may be larger than the width. The length of the positioning slot 138 may extend parallel with the longitudinal axis of the template 110 and along a direction between the distal end 112 and the proximal end 114. The width of the positioning slot 138 may extend generally perpendicular to the longitudinal axis of the template 110 and along a direction between the dorsal side 116 and the plantar side 118. The guide wire 150, as shown in FIGS. 1 and 2, may include a first end 152 and a second end 154 and may be used for positioning the template 110 on the patient's bones, as described in greater detail below with reference to FIGS. 27-45.

As shown in FIGS. 3-6, the template 110 may further include a first alignment guide opening 140 and a second alignment guide opening 142. The first and second alignment guide openings 140, 142 are sized and shaped or configured to couple to the alignment guide apparatus 200. The first alignment guide opening 140 may be, for example, positioned near the distal end 112 between the first distal lobe 124 and the second distal lobe 126. The second alignment guide opening 142 may be, for example, positioned between a mid-point along the longitudinal axis of the template 110 and the first alignment guide opening 140. The second alignment guide opening 142 may be positioned, for example, closer to the dorsal side 116 of the template 110. In addition, the first alignment guide opening 140 may have, for example, a smaller diameter than the second alignment guide opening 142. The alignment guide openings 140, 142 may each extend, for example, through the template 110 from the exterior surface 120 to the interior surface 122.

Figure 11:
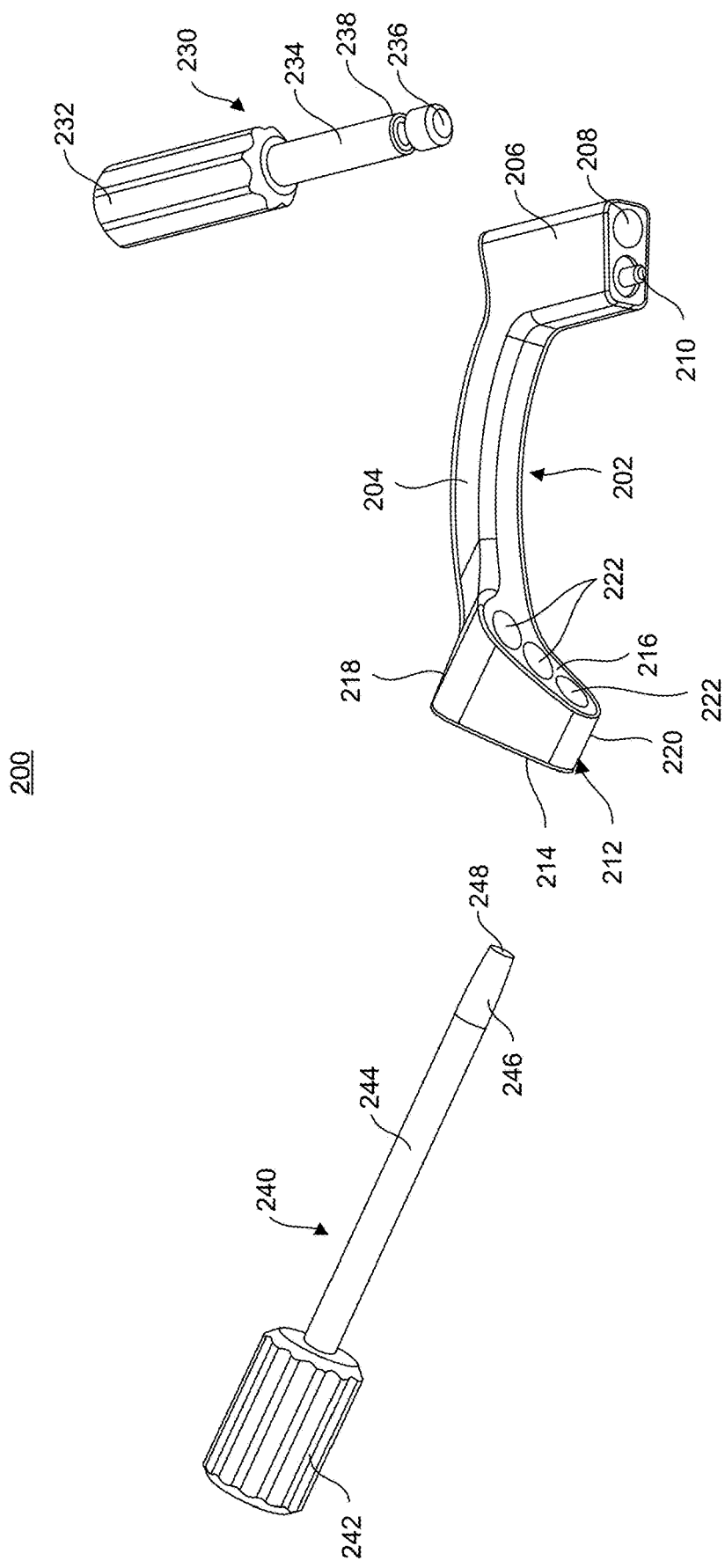
FIG. 11 is an exploded bottom view of an alignment guide apparatus of the bone fusion system of FIG. 1, in accordance with an aspect of the present invention.
Figure 12:
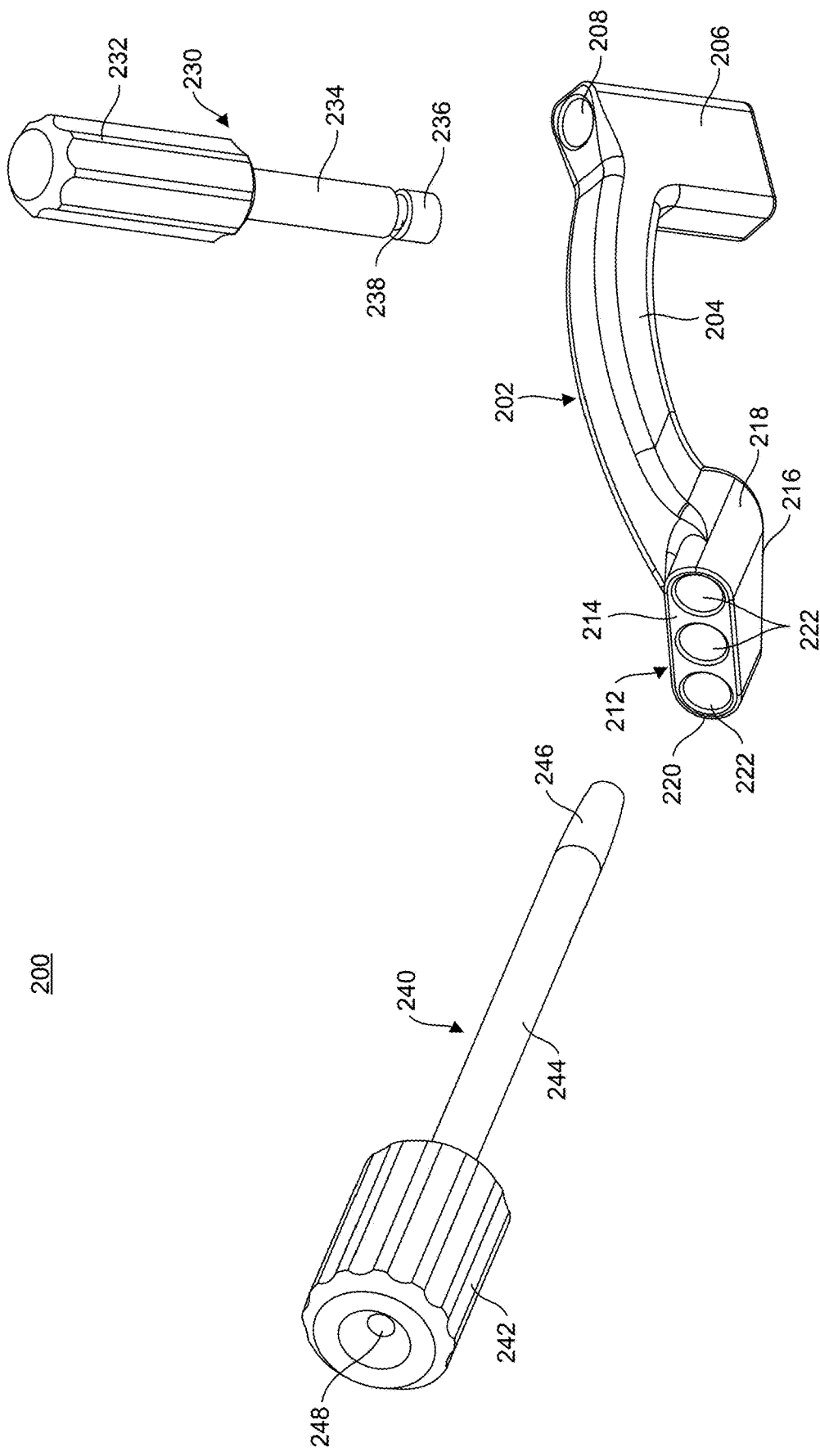
FIG. 12 is an exploded end view of the alignment guide apparatus of FIG. 11, in accordance with an aspect of the present invention.
Figure 13:
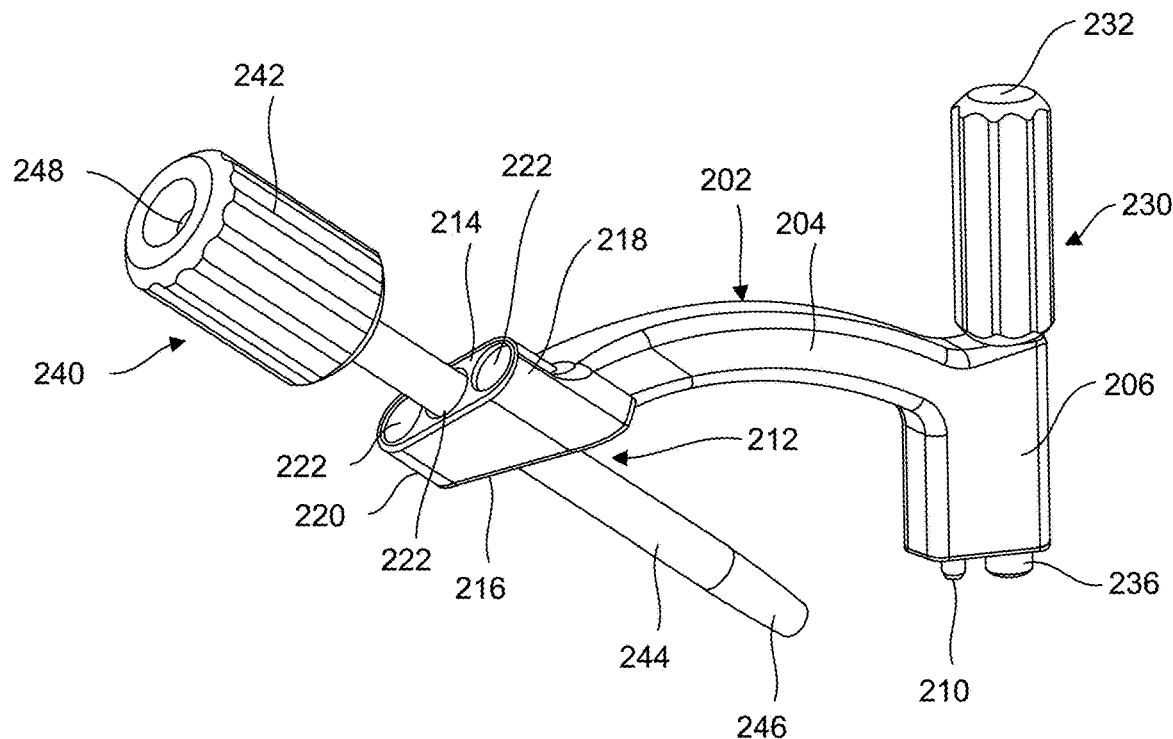
FIG. 13 is an assembled, side perspective view of the alignment guide apparatus of FIG. 11, in accordance with an aspect of the present invention.
Figure 14:
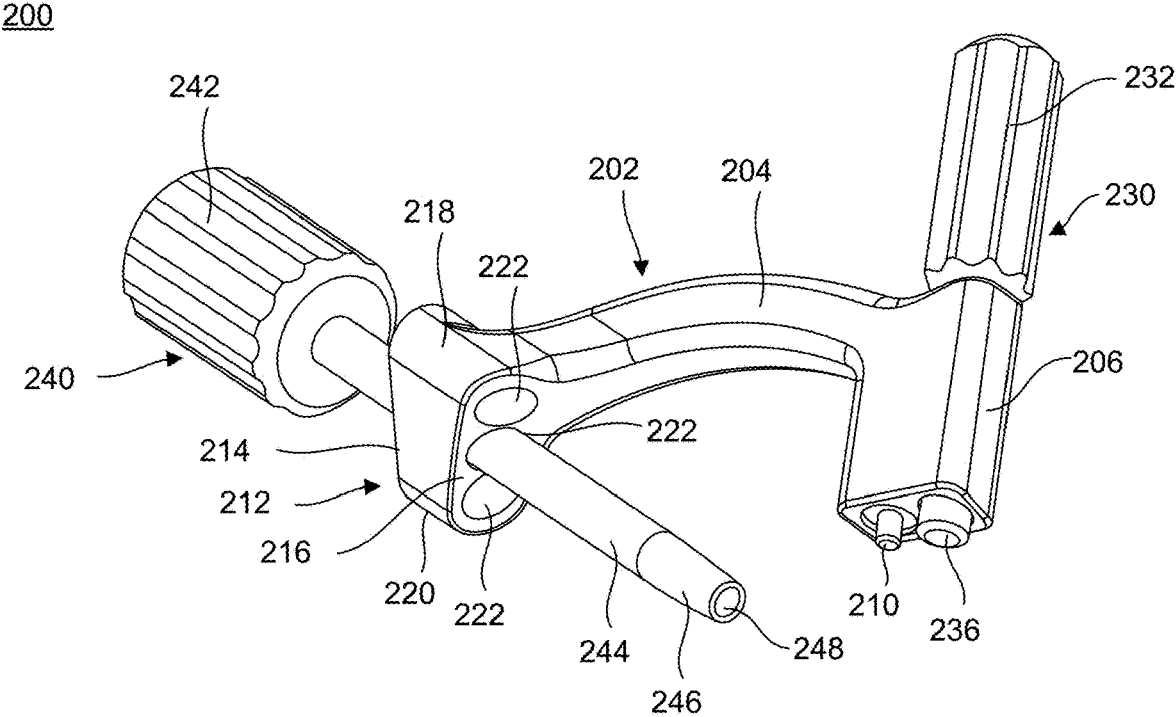
FIG. 14 is a bottom perspective view of the alignment guide apparatus of FIG. 13, in accordance with an aspect of the present invention.
Figure 15:
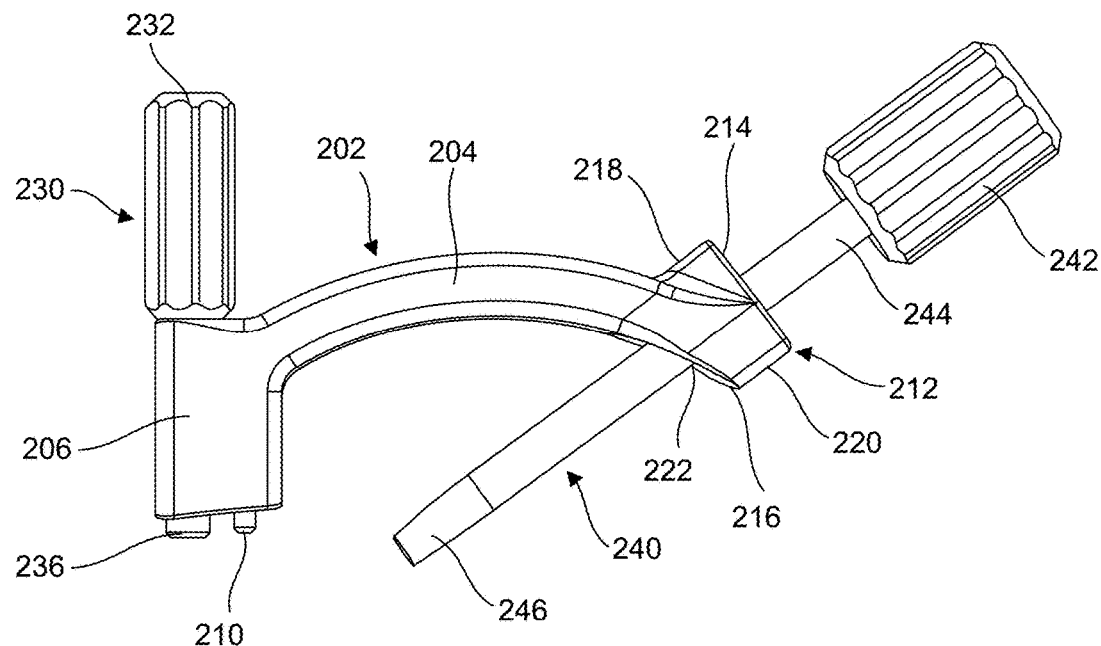
FIG. 15 is a side view of the alignment guide apparatus of FIG. 13, in accordance with an aspect of the present invention.
Figure 16:
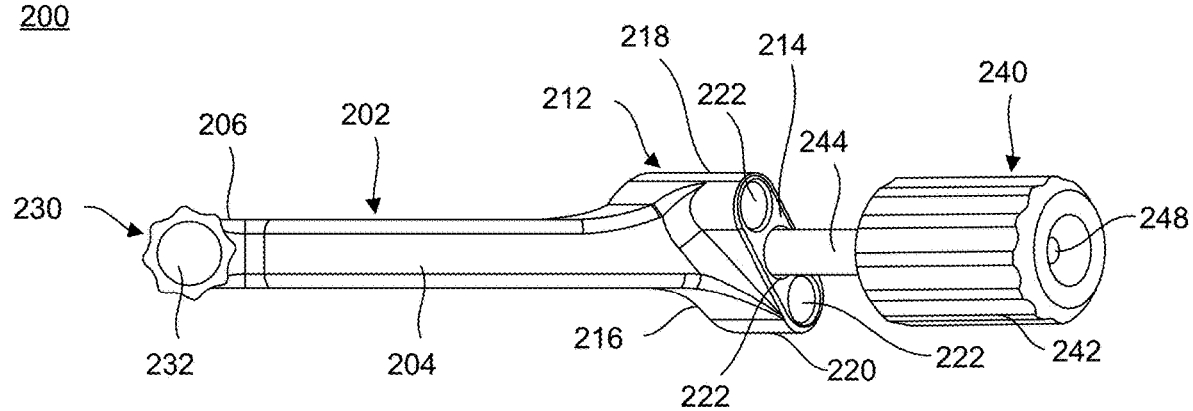
FIG. 16 is a top view of the alignment guide apparatus of FIG. 13, in accordance with an aspect of the present invention.
Figure 18:
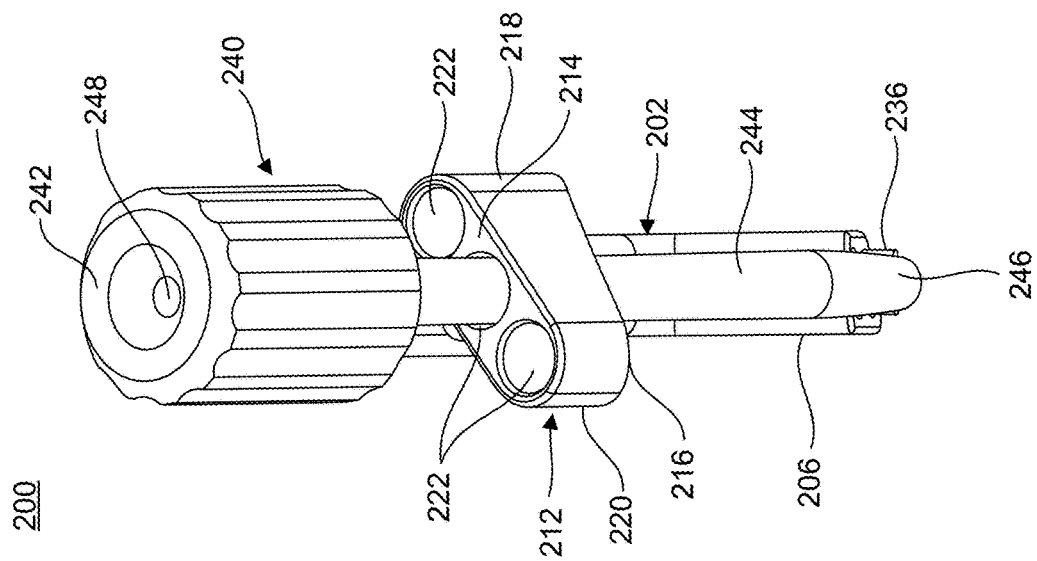
FIG. 18 is a second end view of the alignment guide apparatus of FIG. 13, in accordance with an aspect of the present invention.
Figure 17:
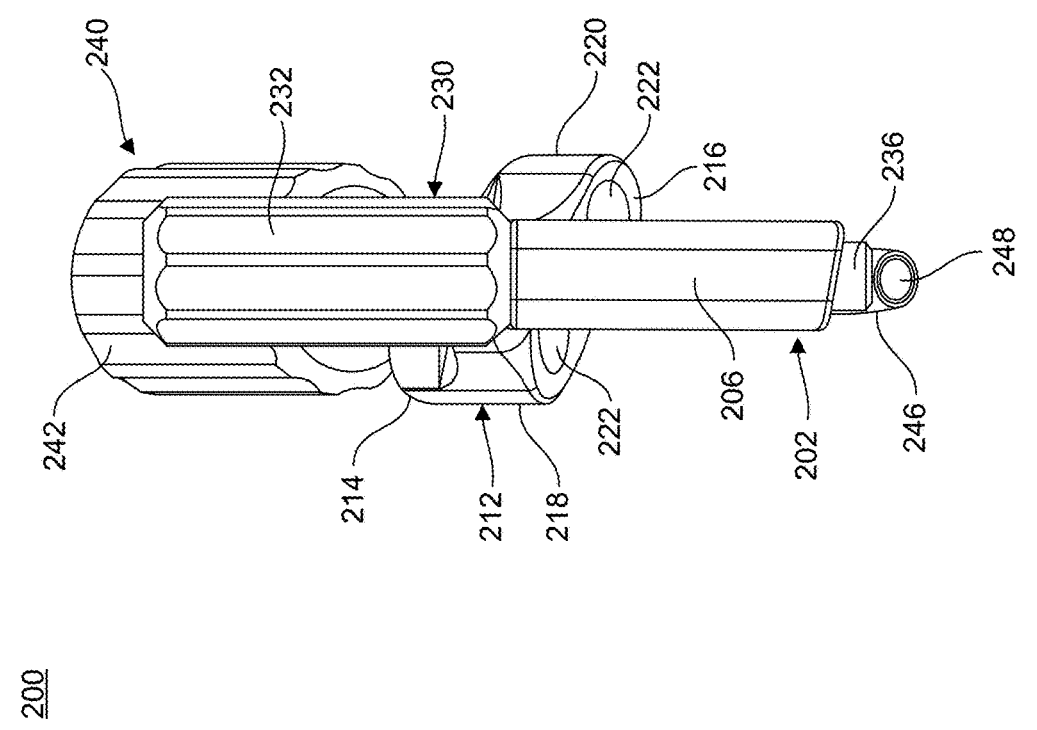
FIG. 17 is a first end view of the alignment guide apparatus of FIG. 13, in accordance with an aspect of the present invention.
Figure 19:
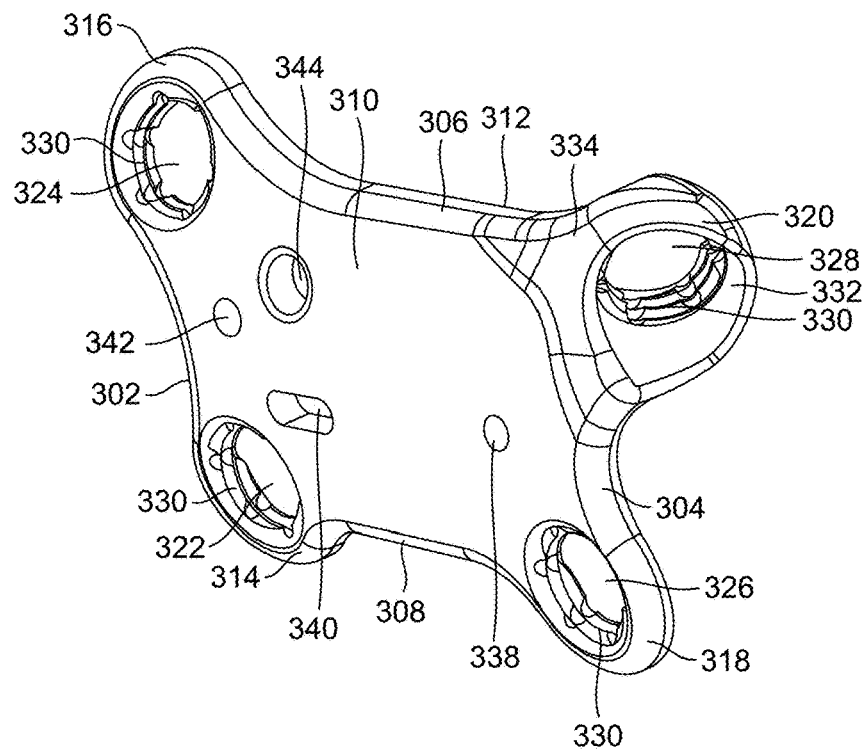
FIG. 19 is a first side perspective view of a plate of the bone fusion system of FIG. 1, in accordance with an aspect of the present invention.

As shown in FIGS. 11-18, the alignment guide apparatus 200 may include a body or alignment guide 202, a fixation member 230, a guide pin protector 240, a guide wire or pin (not shown), and the fastener 250 of FIGS. 1 and 2. The body 202 may include an arm 204 with an attachment portion 206 at a first end and an alignment portion 212 at a second end. The arm 204 may be, for example, curved along the longitudinal axis of the body 202 from the attachment portion 206 to the alignment portion 212. The body 202 may also include a through hole 208 in the attachment portion 206 of the body 202, as seen in FIGS. 11 and 12. Further, the body 202 may include an alignment protrusion 210 extending away from the attachment portion 206, as shown in FIGS. 11 and 13-15, for engaging the first alignment guide opening 140 of the template 100 of FIGS. 1-6 or an opening 342 in a bone plate 300 of FIGS. 1, 2, 19-22 and 25. The alignment protrusion 210 may be used to position the bone plate alignment guide apparatus 200 on the template 110 or a bone plate 300. The through hole 208 may be positioned, for example, adjacent to the alignment protrusion 210, as shown in FIGS. 11 and 13-15.

The alignment portion 212 may include, for example, a first end 214 opposite a second end 216 and a first side 218 opposite a second side 220, as shown in FIGS. 11-14, 16 and 18. The second end 216 may be, for example, curved perpendicular to the longitudinal axis of the alignment portion 212 or along the longitudinal axis of the body 202. The alignment portion 212 may be, for example, angled from the first side 218 to the second side 220 forming a tapered alignment portion 212. The tapered alignment portion 212 may be formed, for example, by tapering the second end 216 and having a straight first end 214 or, alternatively, by tapering both the first and second ends 214, 216. The first side 218 of the alignment portion 212 may be larger than the second side 220. The alignment portion 212 of the body 202 may be, for example, a variable hole alignment portion, and may include a plurality of holes or through holes 222, as shown in FIGS. 2, 11-14, 16 and 18. The plurality of holes 222 may be positioned in a linear arrangement with a center hole, a right hole to the right of the center hole, and a left hole to the left of the center hole. The plurality of holes 222 may be, for example, straight or angled to a desired insertion position relative to the arm 204 of the body 202. By way of specific example, the left hole and right hole may each be slightly angled toward the center hole such that each of the side holes converge toward the center hole. More specifically, the extended target pathways of each of the plurality of holes 222 may, for example, intersect at a point along the pathway of the center hole 222 prior to reaching a target bone, for example, the navicular bone.

The fixation member 230 may include a knob portion 232 and a shaft portion 234 with an engagement portion or region 236 for engaging a bone plate, for example, bone plate 300 of FIGS. 1, 2, and 19-26. The engagement portion 236 may be, for example, threaded to engage corresponding threads in an opening 344 in the bone plate 300, deformable to be removably press fit into the opening 344 in the bone plate 300, or similar configurations that achieve a coupling of the guide apparatus 200 to a second alignment guide opening 344 of the bone plate 300. In addition, the engagement portion 236 may be, for example, threaded to engage corresponding threads in the second alignment guide opening 142 in the template 110, deformable to be removably press fit into the opening 142 in the template 110, or similar configurations that achieve a coupling of the guide apparatus 200 to the second alignment guide opening 142 of the template 110. The shaft portion 234 of the fixation member 230 may also include a groove or recessed region 238 positioned adjacent to the engagement portion 236. The guide wire (not shown) may be of the type described above with reference to guide wire 150, which will not be described again here for brevity sake.

The guide pin protector or tissue protector 240, as shown in FIGS. 11-18, may include a handle portion 242 at a first end and a shaft 244 extending away from the handle portion 242 to a tip 246 at a second end. The shaft 244 may taper at the second end to form the tip 246. The guide pin protector 240 may also include a through hole 248 extending from the first end to the second end to enable a guide wire (not shown) to pass through the tissue protector 240 and into the patient's bone.

The compression screw, lag screw, compression fastener, or lag fastener 250 may include a head portion 252 and a shaft or shank portion 254, as shown in FIGS. 1 and 2. The shaft portion 254 may include an upper portion 256 and a threaded portion 258. The shaft portion 254 may extend away from the head portion 252. The upper portion 256 may be, for example, smooth or alternatively may be threaded along at least a portion of the upper portion 256. The compression screw 250 may also include a through hole 260 extending from the proximal end to the distal end of the screw 250.

Figure 30:
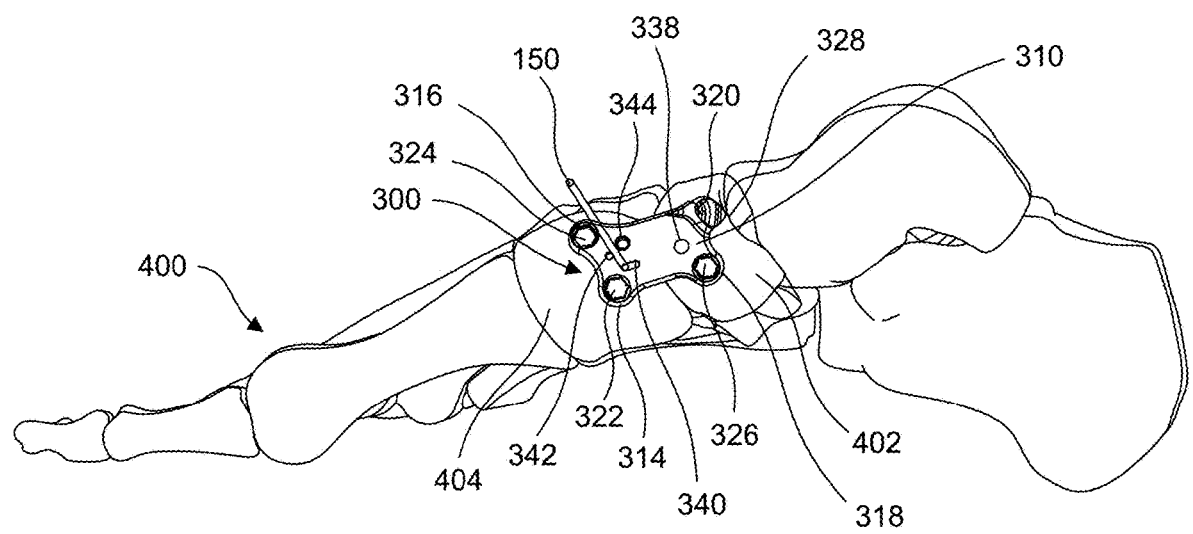
FIG. 30 is a perspective view of the foot of FIG. 29 with the plate of FIG. 19 positioned on the foot, in accordance with an aspect of the present invention.

As shown in FIGS. 1 and 2, the drill bit 270 may include a shaft portion 272 with a drill engagement member 274 at the first end and a cutting member 276 at the second end. The drill engagement member 274 may be sized and shaped or configured to be inserted into an instrument (not shown) to rotate the drill bit 270. The instrument (not shown) may be, for example, a handle allowing for manual rotation or a drill allowing for power rotation. The cutting member 276 may include a cutting edge or surface 278 to form a recess into a bone for receiving a plate 300, as shown in FIG. 30.

Referring now to FIGS. 19-26, the plate 300 is shown. The plate 300 may include a first or distal end 302 opposite a second or proximal end 304, a top or dorsal side 306 opposite a bottom or plantar side 308, and an exterior surface 310 opposite an interior or bone facing surface 312. The plate 300 may also include a first distal or plantar lobe, ear, or tab 314 extending away from the portion of the plate 300 where the distal end 302 contacts the plantar side 308, as shown in FIGS. 19-22. The first distal lobe 314 of the plate 300 may also include a first distal lobe opening 322. The first distal lobe opening 322 may include, for example, locking threads 330, as shown in FIGS. 19-22. The plate 300 may further include a second distal or dorsal lobe, ear, or tab 316 extending away from the portion of the plate 300 where the distal end 302 contacts the dorsal side 306, as shown in FIGS. 19-22. The second distal lobe 316 of the plate 300 may also include a second proximal lobe opening 324 with, for example, locking threads 330. In addition, the plate 300 may include a first proximal or plantar lobe, ear, or tab 318 extending away from the portion of the plate 300 where the proximal end 304 contacts the plantar side 308, as shown in FIGS. 19-22. The first proximal lobe 318 of the plate 300 may also include a first proximal lobe opening 326 with, for example, locking threads 330. Further, the plate 300 may include a second proximal or dorsal lobe, ear, or tab or screw housing 320 positioned where the proximal end 304 contacts the dorsal side 306, as shown in FIGS. 19-22. The second proximal lobe 320 of the plate 300 may also include a second proximal lobe opening 328 with, for example, locking threads 330.

Figure 20:
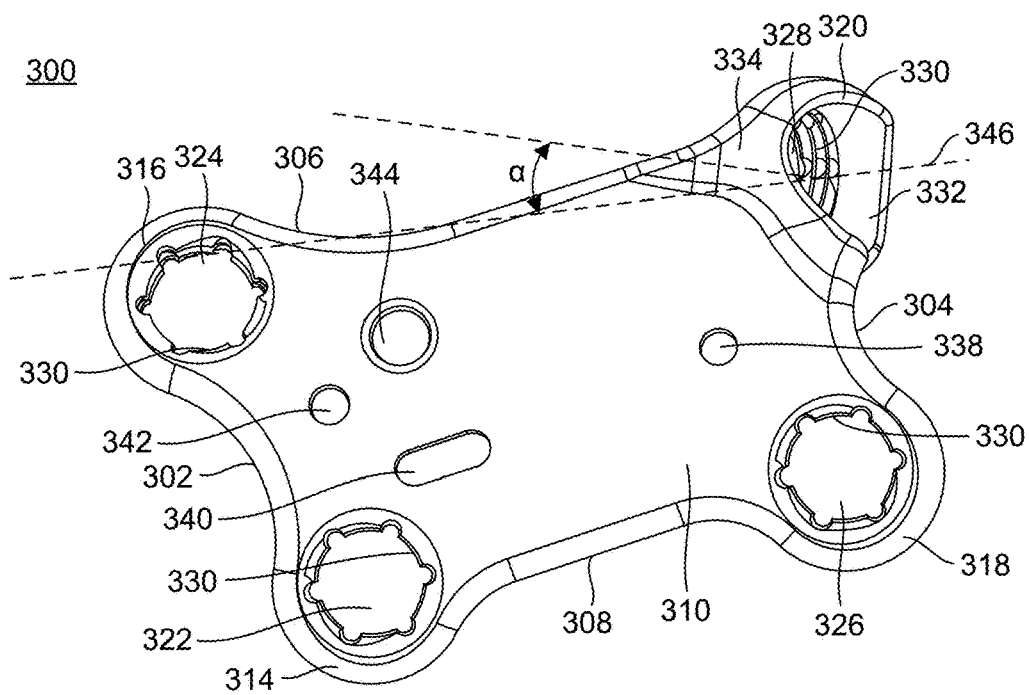
FIG. 20 is a first side view of the plate of FIG. 19, in accordance with an aspect of the present invention.
Figure 21:
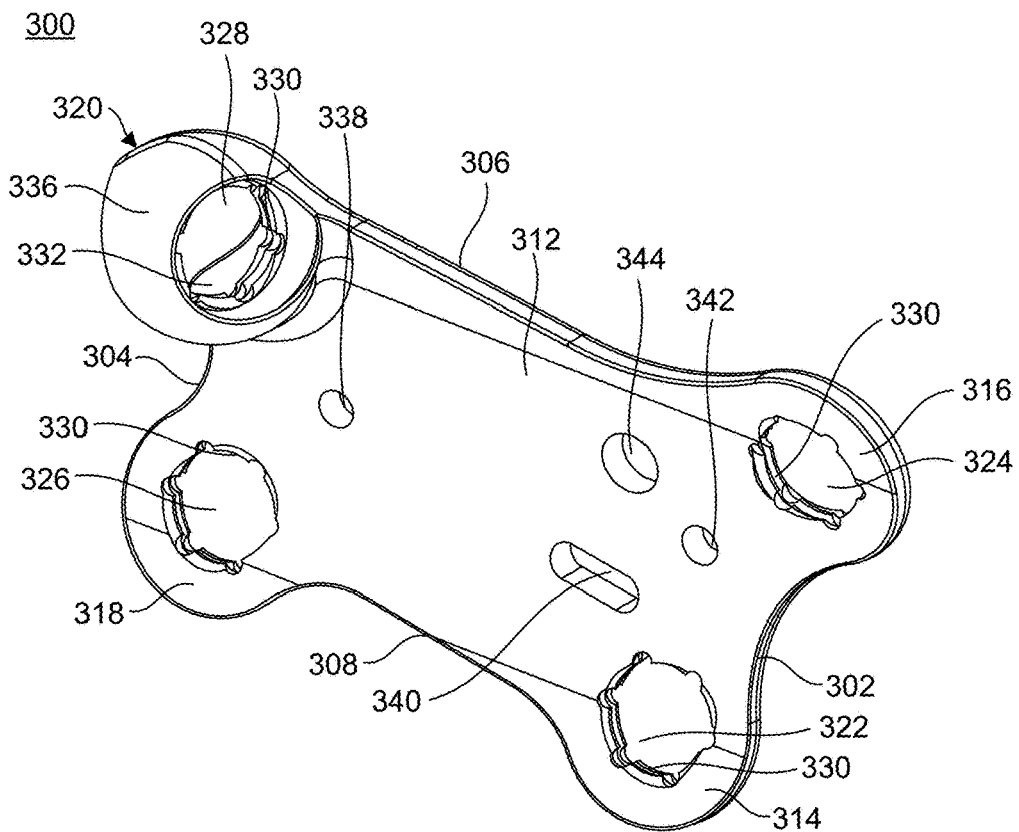
FIG. 21 is a second side perspective view of the plate of FIG. 19, in accordance with an aspect of the present invention.
Figure 22:
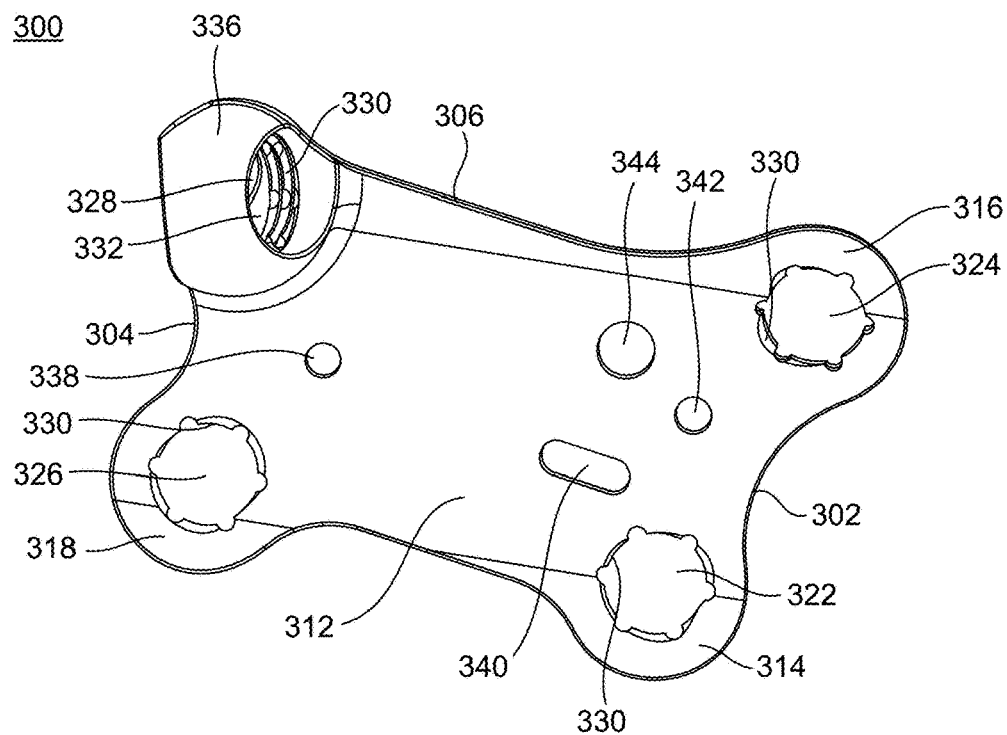
FIG. 22 is a second side view of the plate of FIG. 19, in accordance with an aspect of the present invention.
Figure 23:
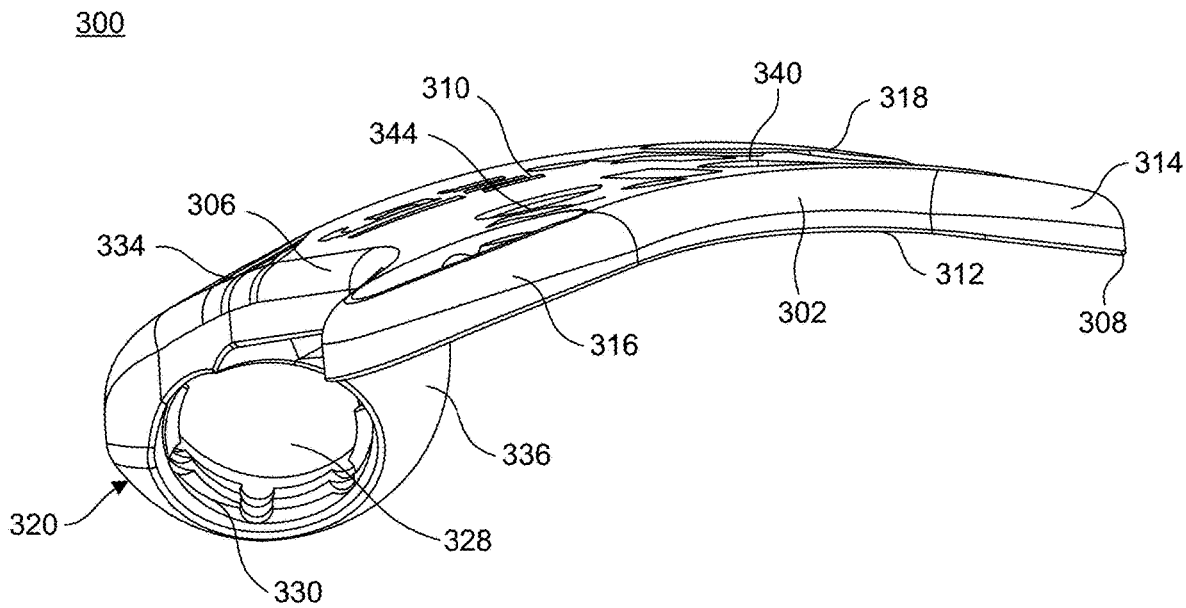
FIG. 23 is a distal end view of the plate of FIG. 19, in accordance with an aspect of the present invention.
Figure 24:
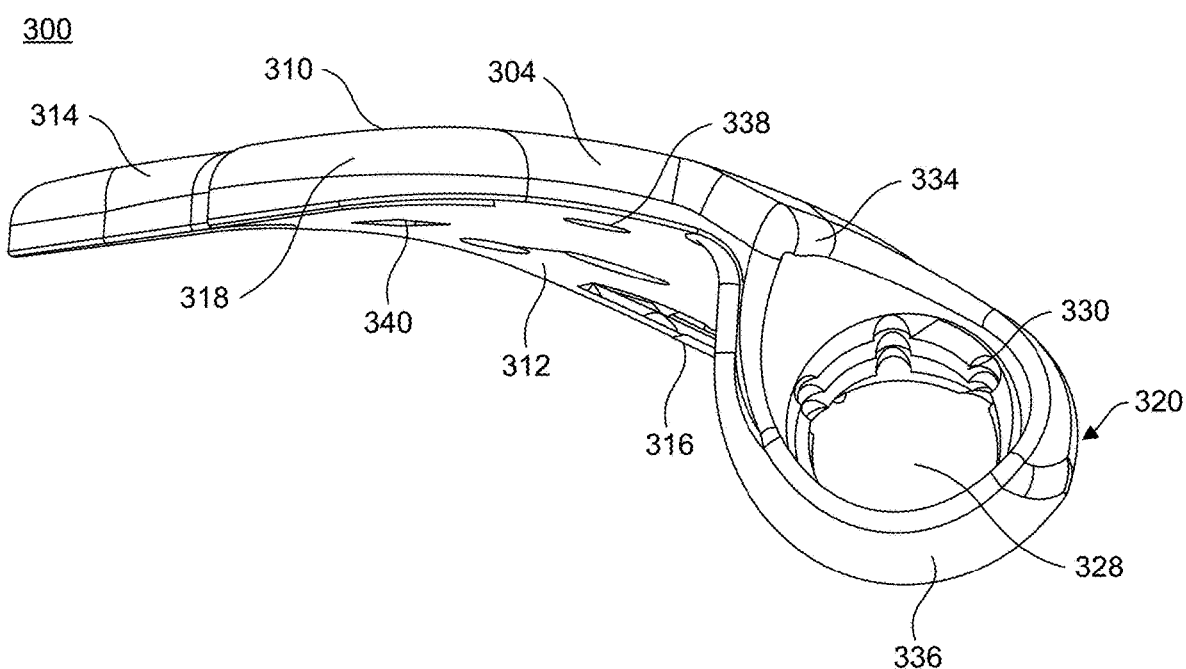
FIG. 24 is a proximal end view of the plate of FIG. 19, in accordance with an aspect of the present invention.
Figure 25:
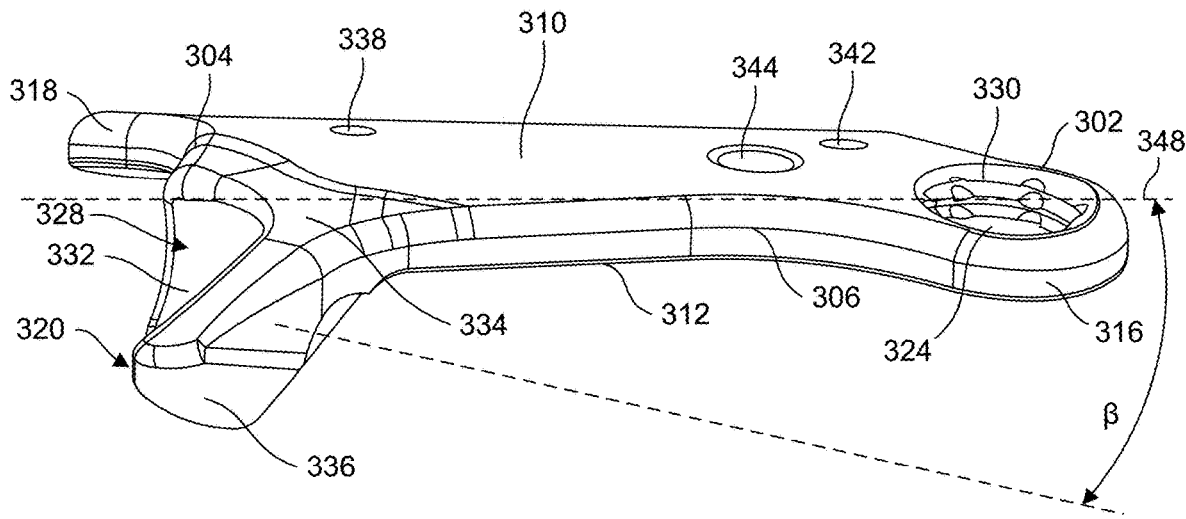
FIG. 25 is a dorsal side view of the plate of FIG. 19, in accordance with an aspect of the present invention.
Figure 26:
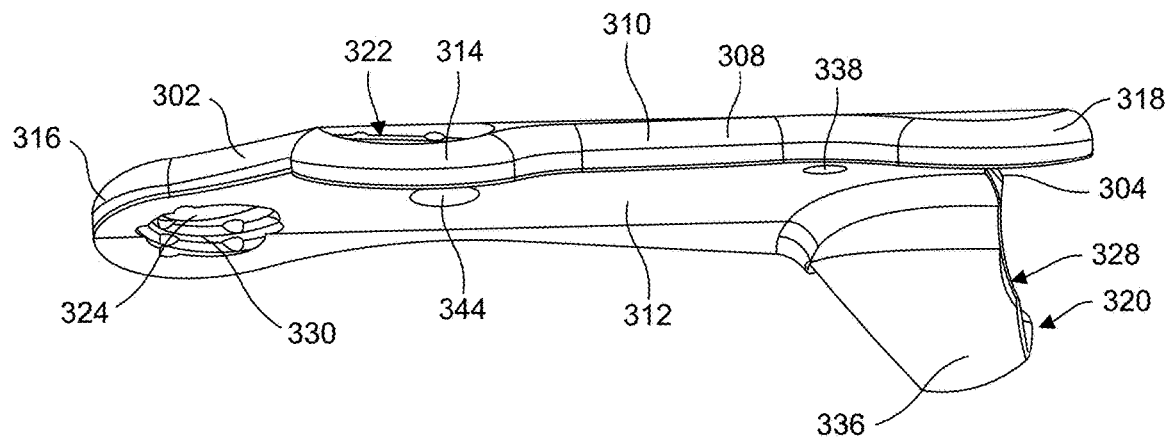
FIG. 26 is a plantar side view of the plate of FIG. 19, in accordance with an aspect of the present invention.

As shown in FIGS. 19-26, the second proximal lobe 320 may include an extended smooth region or lip portion 332 positioned on the surface of the opening 328 between the exterior surface 310 and the locking threads 330. In addition, the second proximal lobe 320 includes an angled portion 334 positioning the opening 328 at an angle, for example, an oblique angle relative to the plate 300. Specifically, the second proximal or dorsal lobe 320 may be, for example, angled relative to the exterior surface 310 of the plate 300. The second proximal lobe 320 may also include a wide bone contacting portion 336 on the interior surface 312 of the plate 300. As shown in FIGS. 21-26, the interior surface 312 of the second proximal lobe 320 may have, for example, a semi-circular shape to engage a recessed portion of a patient's bone, as described in greater detail below with reference to FIGS. 27-45. The central axis of the opening 328 of the second proximal lobe 320 may include, for example, a compound angle including a first angle α and a second angle β. As shown in FIG. 20, the first angle α may be the angle of the central axis of the opening 328 from the horizontal plane 346. The first angle α may range from, for example, approximately 1° to approximately 25°, more preferably, approximately 13°. As shown in FIG. 25, the second angle β may be the angle of the central axis of the opening 328 from the top surface or dorsal plane 348. The second angle β may range from, for example, approximately 5° to approximately 75°, more preferably, approximately 28°.

With continued reference to FIGS. 19-26, the plate 300 may include an alignment opening 338 and a positioning slot 340 for receiving, for example, guide wires, k-wires, olive wires, pins, or alignment wires 150. The alignment opening 338 may be positioned, for example, near the proximal end 304 of the plate 300 and near a mid-point between the dorsal side 306 and plantar side 308 of the plate 300. The alignment opening 338 may extend through the plate 300 from the exterior surface 310 to the interior surface 312. The positioning slot 340 may be positioned, for example, between a mid-point along the longitudinal axis of the plate 300 and the distal end 302. The positioning slot 340 may have, for example, a length and a width and the length may be larger than the width. The length of the positioning slot 340 may extend parallel to the longitudinal axis of the plate 300 between the distal end 302 and proximal end 304. The width of the positioning slot 340 may extend generally perpendicular to the longitudinal axis of the plate 300 between the dorsal side 306 and the plantar side 308. A guide wire 150, as shown in FIGS. 1 and 2, inserted into the positioning slot 340 may be used for aligning the plate 300 on the patient's bones based on the trialed position of the template 110, as described in greater detail below with reference to FIGS. 27-45. The guide wire 150 and positioning slot 340 may also be used to constrain the position of the plate 300 as an external compression screw, for example, screw 250 of FIGS. 1 and 2 enters the patient's bones from the medial cuneiform to the navicular bone, as described in greater detail below with reference to FIGS. 27-45.

As shown in FIGS. 19-26, the plate 300 may further include a first alignment guide opening 342 and a second alignment guide opening 344. The first and second alignment guide openings 342, 344 are sized and shaped or configured to couple to the alignment guide apparatus 200. The first alignment guide opening 342 may be, for example, positioned near the distal end 302 between the first distal lobe 314 and the second distal lobe 316. The second alignment guide opening 344 may be, for example, positioned between a mid-point along the longitudinal axis of the plate 300 and the first alignment guide opening 342. The second alignment guide opening 344 may be positioned, for example, closer to the dorsal side 306 of the plate 300. In addition, the first alignment guide opening 342 may have, for example, a smaller diameter than the second alignment guide opening 344. The alignment guide openings 342, 344 may each extend, for example, through the plate 300 from exterior surface 310 to the interior surface 312.

Figure 27:
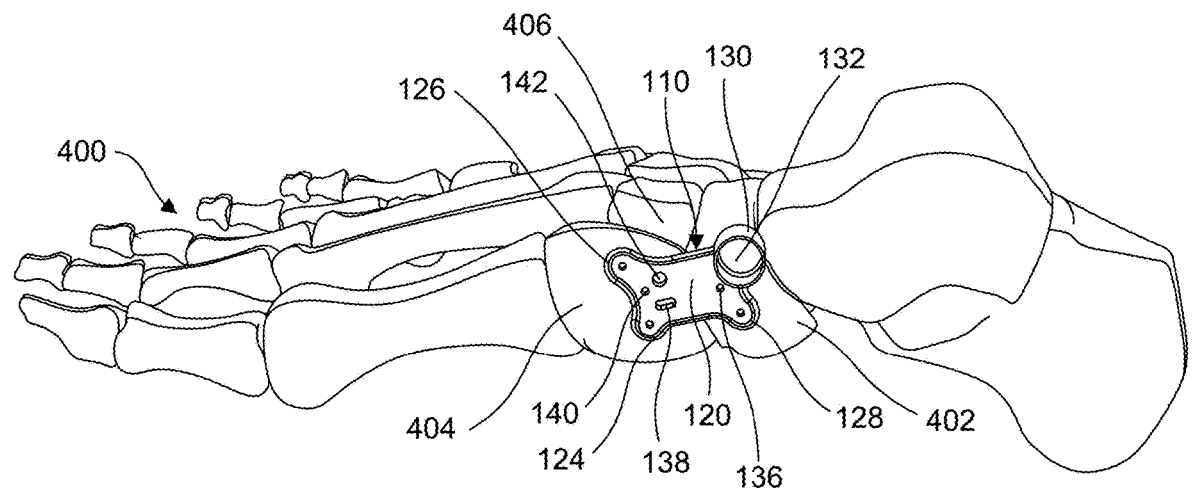
FIG. 27 is a perspective view of the implant template of FIG. 3 positioned on a foot, in accordance with an aspect of the present invention.
Figure 28:
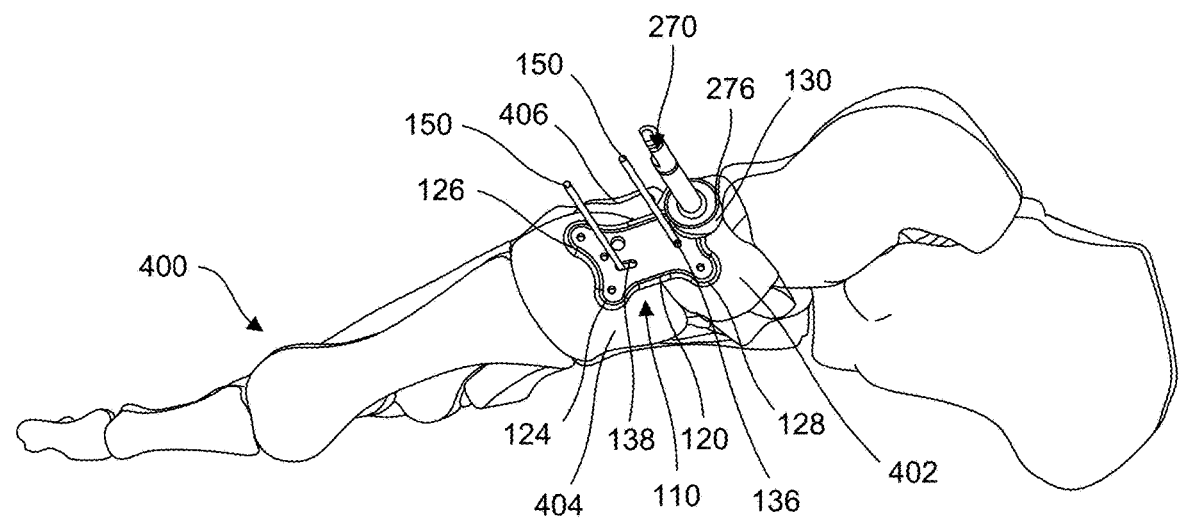
FIG. 28 is a perspective view of the foot of FIG. 27 with two guide wires and a drill bit inserted into the implant template of FIG. 3, in accordance with an aspect of the present invention.
Figure 29:
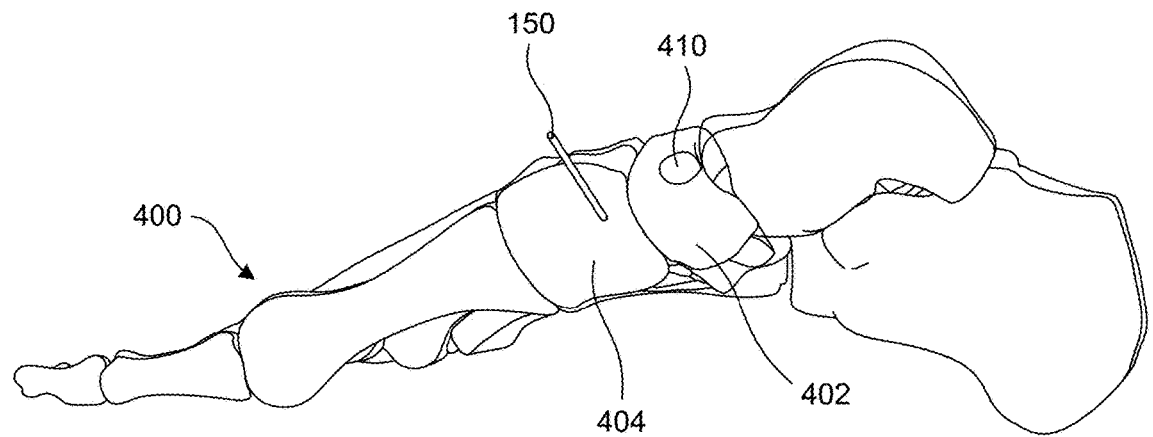
FIG. 29 is a perspective view of the foot of FIG. 28 with one guide wire, the implant template and the drill bit removed from the foot, in accordance with an aspect of the present invention.

Methods of using the bone fusion system 100 are shown in FIGS. 27-45. Although the methods of FIGS. 27-45 are shown and described with respect to the navicular-cuneiform joint, it is also contemplated that the methods may be used on any bone joint in the body. The methods may include making an incision over a joint, for example, a navicular-cuneiform joint in-between the tibialis posterior and tibialis anterior tendons. Next, the method may include preparing the joint for fusion, which may include, for example, removing the cartilage from both ends of the bones. Once the joint is are prepared, a template 110 may be selected that corresponds to the size of the plate 300 that best fits the patient's anatomy. As shown in FIG. 27, the template 110 may then be attached to the navicular bone 402 using, for example, an olive wire, guide wire, k-wire, or the like 150 (as shown in FIG. 28) inserted into the alignment opening 136. As also shown in FIG. 28, a second k-wire, guide wire, or the like 150 may be inserted through the positioning slot 138 into the medial cuneiform 404. The template 110 may then be used in combination with the drill bit 270 to create a recessed region 410 in the navicular bone 402, as shown in FIG. 29. Specifically, the recessed region 410 may be formed by inserting the drill bit 270 into the drill opening 132 in the proximal drill guide member 130, as shown in FIG. 28, and drilling to remove bone material from the navicular bone 402. The cutting member 276 of the drill bit 270 may include depth markings (not shown) on the exterior surface of the cutting member 276, which may be, for example, solid lines, dashed lines or some combination that may extend around the entire circumference of the cutting member 276 or only a portion of the circumference of the cutting member 276. During the insertion of the cutting member 276 of the drill bit 270 into the drill opening 132 of the implant template 110, the depth markings (not shown) provide, for example, an indication of how deep the bone should be reamed in order to receive the plate 300.

After the recessed region 410 is formed, the olive wire 150 may be removed from the alignment opening 136 and the navicular bone 402. Next, the template 110 may be slid off the medial cuneiform 404 and the navicular bone 402 leaving the k-wire 150 which was inserted through the positioning slot 138, as shown in FIG. 29. Once the recessed region 410 is formed and the template 110 removed from the bones 402, 404, the positioning slot 340 of a plate 300 may be inserted over the k-wire 150 and the plate 300 may be slid down the k-wire 150 and aligned on the bones 402, 404, as shown in FIG. 30. The second proximal lobe 320 of the plate 300 may be aligned into the recessed hole 410 in the navicular bone 402, as shown in FIG. 30.

Figure 31:
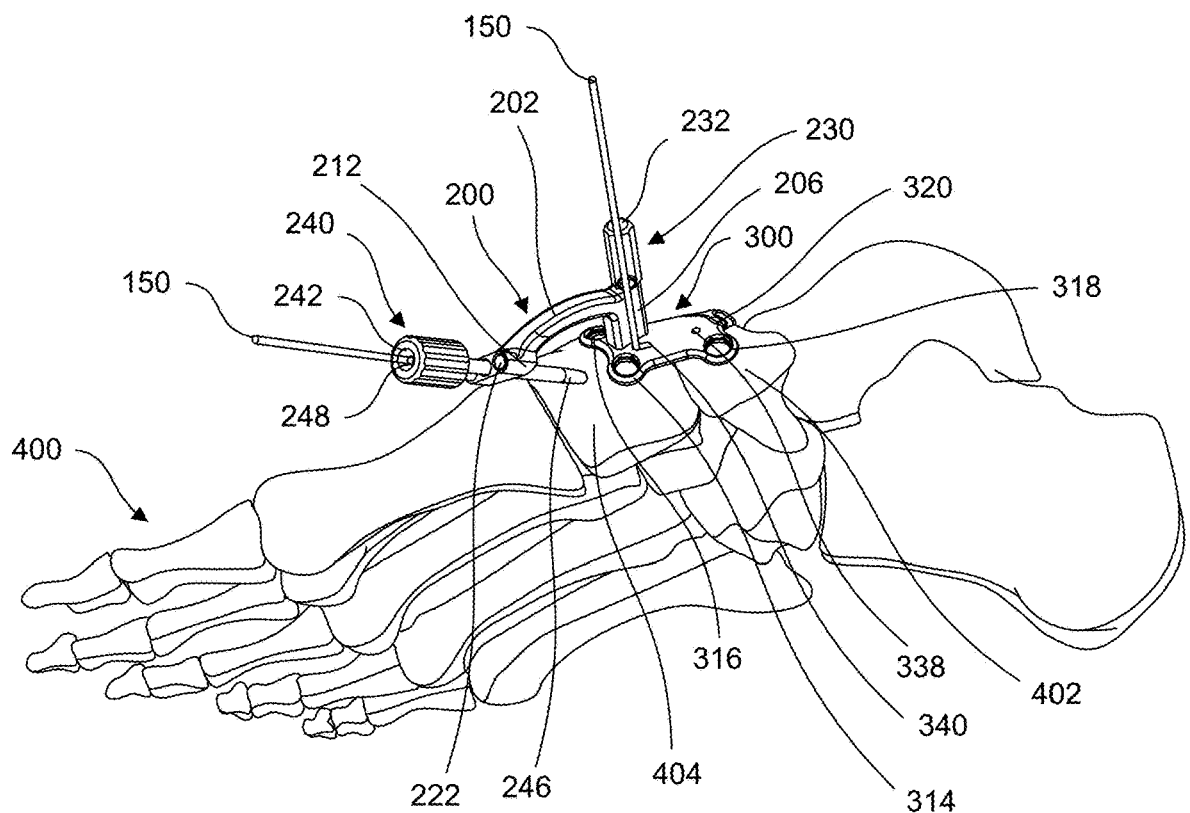
FIG. 31 is an anterior-plantar perspective view of the foot of FIG. 30 with the alignment guide apparatus of FIG. 11 coupled to the plate, in accordance with an aspect of the present invention.

In one embodiment, as shown in FIGS. 31-36, the method may further include coupling the alignment guide apparatus 200 to the alignment guide openings 342, 344 of the plate 300, as shown in FIG. 31. Specifically, the attachment portion 206 of the alignment guide portion or body 202 may be aligned with the alignment guide openings 342, 344 on the plate 300. The alignment protrusion 210 of the attachment portion 206 may be inserted into the first alignment guide opening 342 and the body 202 may be placed in a desired position. Next, the fixation member 230 may be inserted into the through hole 208 in the body 202 and the engagement portion 236 of the fixation member 230 may be coupled to the second alignment guide opening 344 of the plate 300. After the body 202 is secured to the plate 300, the guide pin protector 240 may be inserted into one of the through holes 222 and positioned to contact the medial cuneiform 404, as shown in FIG. 31.

Figure 32:
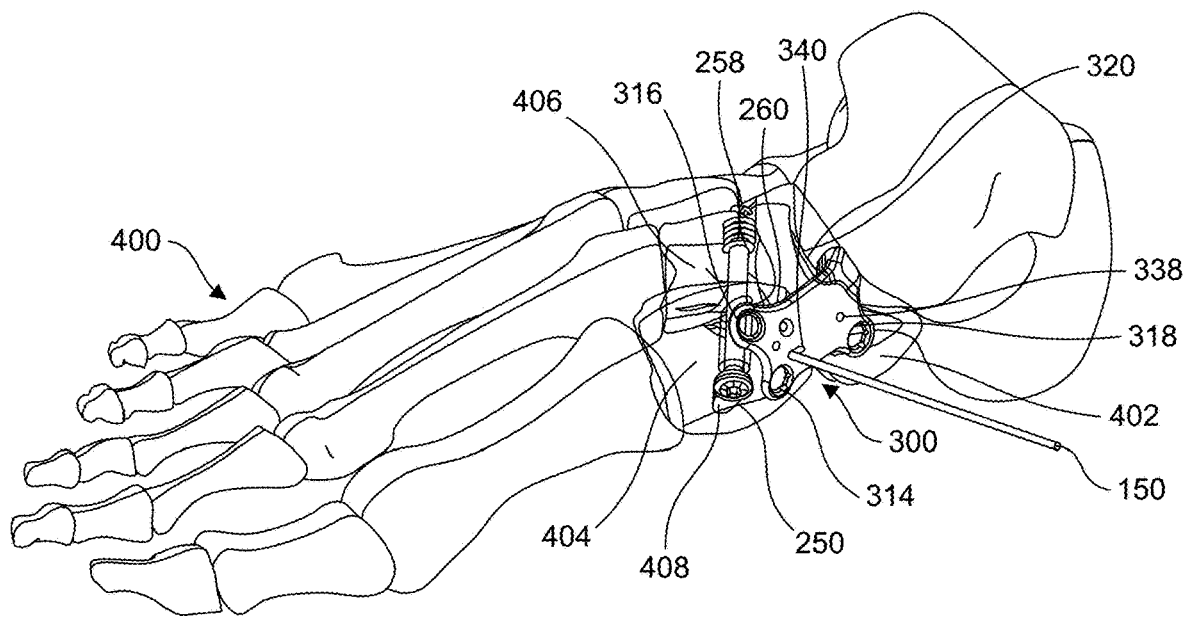
FIG. 32 is an anterior-dorsoplantar perspective view of the foot of FIG. 31 with the alignment guide apparatus removed and a compression fastener of the bone fusion system of FIG. 1 inserted into the foot, in accordance with an aspect of the present invention.

After the guide pin protector 240 is positioned on the medial cuneiform 404, a k-wire, for example, k-wire 150 may be inserted through the through hole 248 in the tissue protector 240 and into the medial cuneiform 404, as shown in FIG. 31. Next, the tissue protector 240, the fixation member 230 and the body 202 may be removed leaving the two k-wires 150 inserted into the medial cuneiform 404. After the alignment guide apparatus 200 is removed, a cannulated drill (not shown) may be obtained and inserted over the k-wire 150 which was inserted using the alignment guide apparatus 200. A second drill (not shown) may then be, for example, used to create a recessed or countersunk opening 408 in the medial cuneiform 404, as shown in FIG. 32. Once the recessed opening 408 is drilled, a fastener 250, for example, a cannulated compression screw, cross screw, screw or interfrag, may be inserted over the k-wire 150 and through the patient's medial cuneiform 404 and into at least the navicular bone 402. The fastener 250 is inserted on a trajectory that will not interfere with the trajectories of the bone screws 350, 360, 370, 380 when inserted. The fastener 250 may be, for example, a partially threaded cross screw. After the fastener 250 is inserted, the k-wire 150 that was inserted with the alignment guide apparatus 200, may be removed, as shown in FIG. 32.

Figure 33:
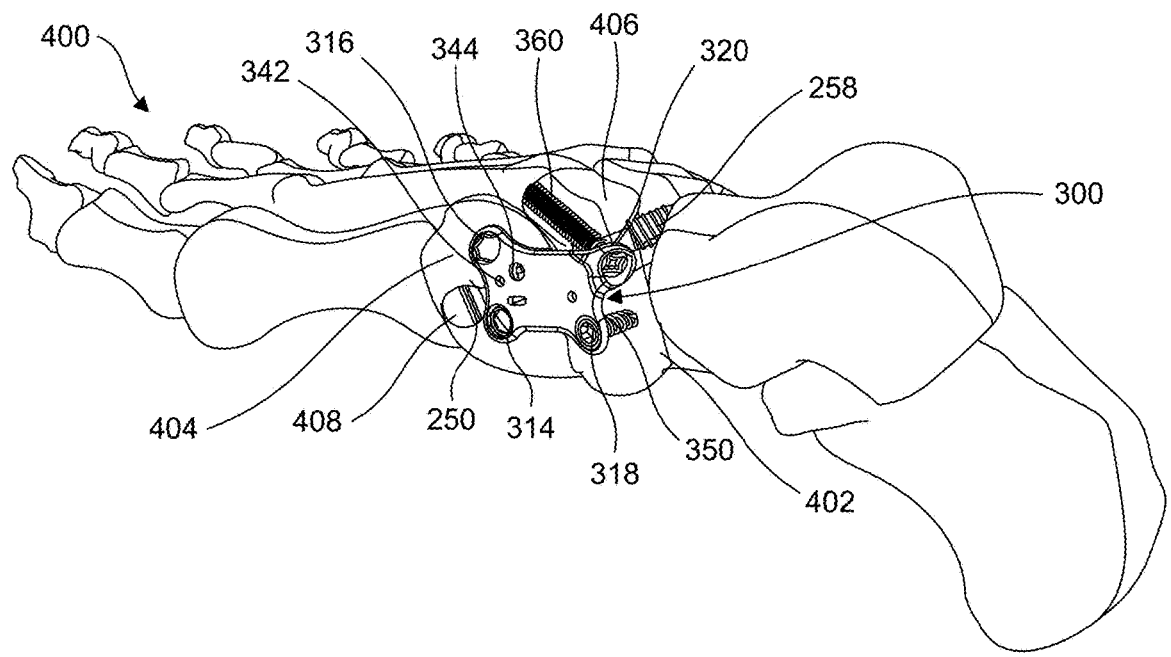
FIG. 33 is a posterior perspective view of the foot of FIG. 32 with two bone fasteners inserted into the proximal end of the plate and the second guide wire removed from the foot, in accordance with an aspect of the present invention.
Figure 34:
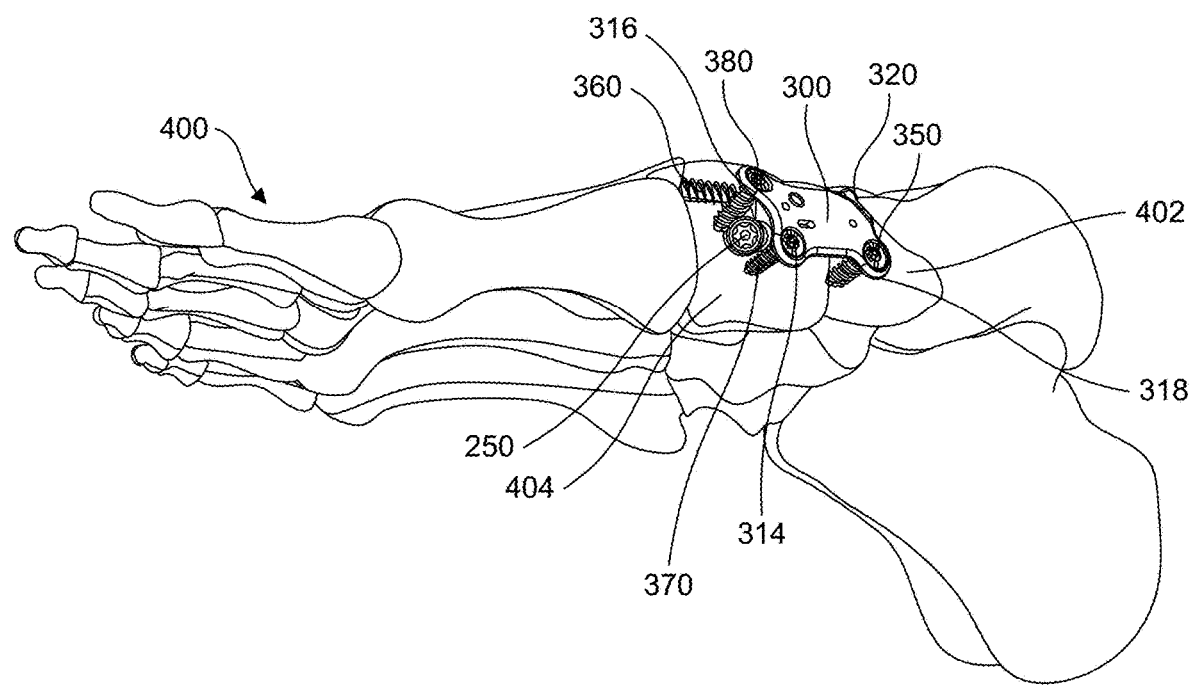
FIG. 34 is an anterior-plantar perspective view of the foot of FIG. 33 with two bone fasteners inserted into the distal end of the plate, in accordance with an aspect of the present invention.
Figure 35:
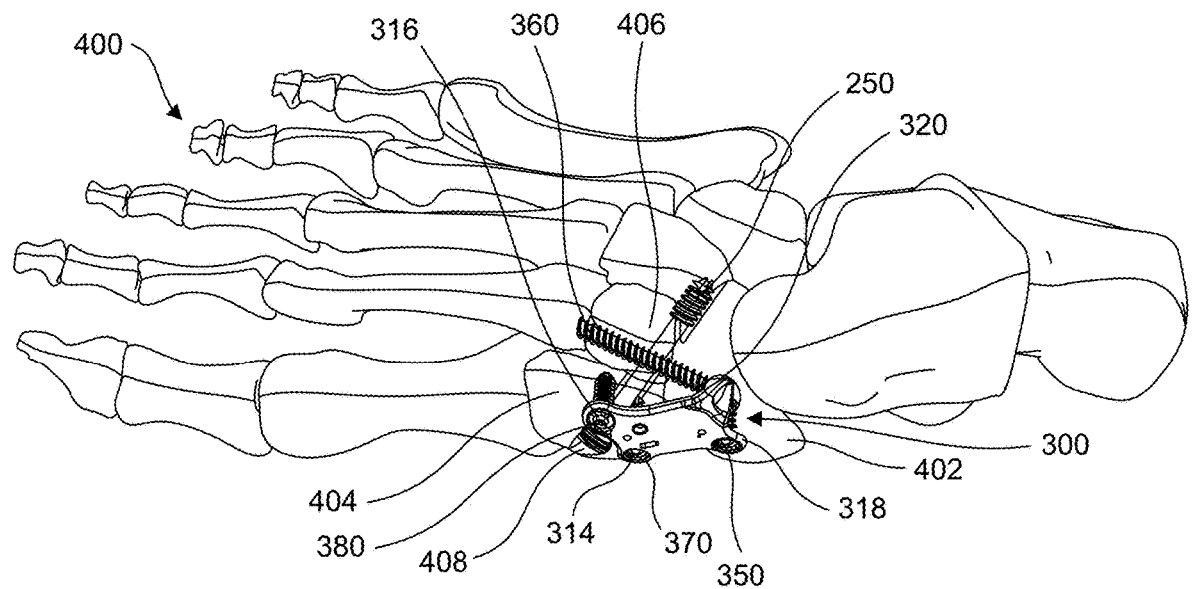
FIG. 35 is a dorsoplantar view of the foot of FIG. 34, in accordance with an aspect of the present invention.
Figure 36:
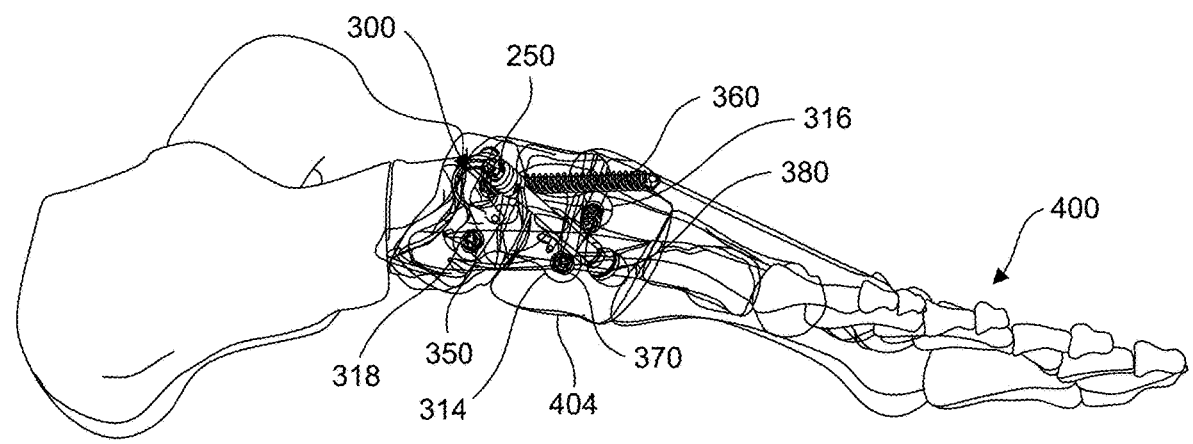
FIG. 36 is a lateral view of the foot of FIG. 34, in accordance with an aspect of the present invention.
Figure 45:
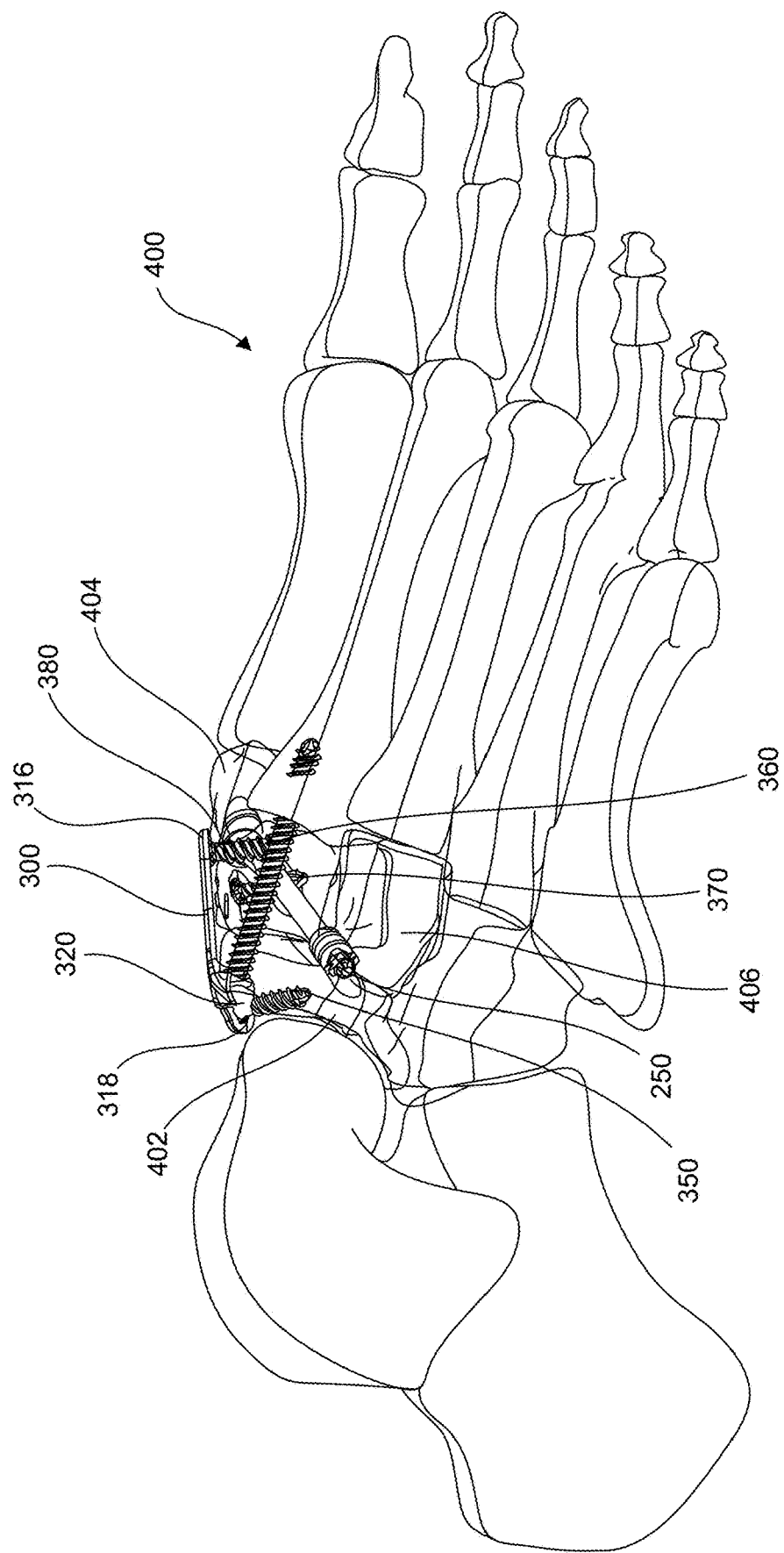
FIG. 45 is a medial view of the foot of FIG. 34, in accordance with an aspect of the present invention.

Referring now to FIG. 33, a fastener or plantar proximal screw 350 may be inserted into the opening 326 in the first proximal lobe 318. The fastener 350 is inserted into the navicular bone 402. Next, a fastener, recessed screw or dorsal proximal screw 360 may be inserted into the opening 328 in the second proximal lobe, angled lobe, or recessed lobe 320, as shown in FIG. 33. The fastener 360 may be inserted through the navicular bone 402 and into the intermediate cuneiform 406. Then, the plantar distal screw or fastener 370 may be inserted into the opening 322 in the first distal lobe 314, as shown in FIG. 34. The plantar distal screw 370 may be inserted into the medial cuneiform 404. In addition, with continued reference to FIG. 34, the dorsal distal screw or fastener 380 may be inserted into the opening 324 in the second distal lobe 316. The dorsal distal screw 380 may be inserted into the medial cuneiform 404. Although the insertion of the fasteners or screws 350, 360, 370, 380 is described in a specific order above, it is also contemplated that the fasteners 350, 360, 370, 380 may be inserted in any alternative order as would be understood by one of ordinary skill in the art. After all of the fasteners 350, 360, 370, 380 are inserted through the plate 300, as shown in FIGS. 35, 36 and 45, the procedure may be completed, and the patient's incision may be closed.

Figure 37:
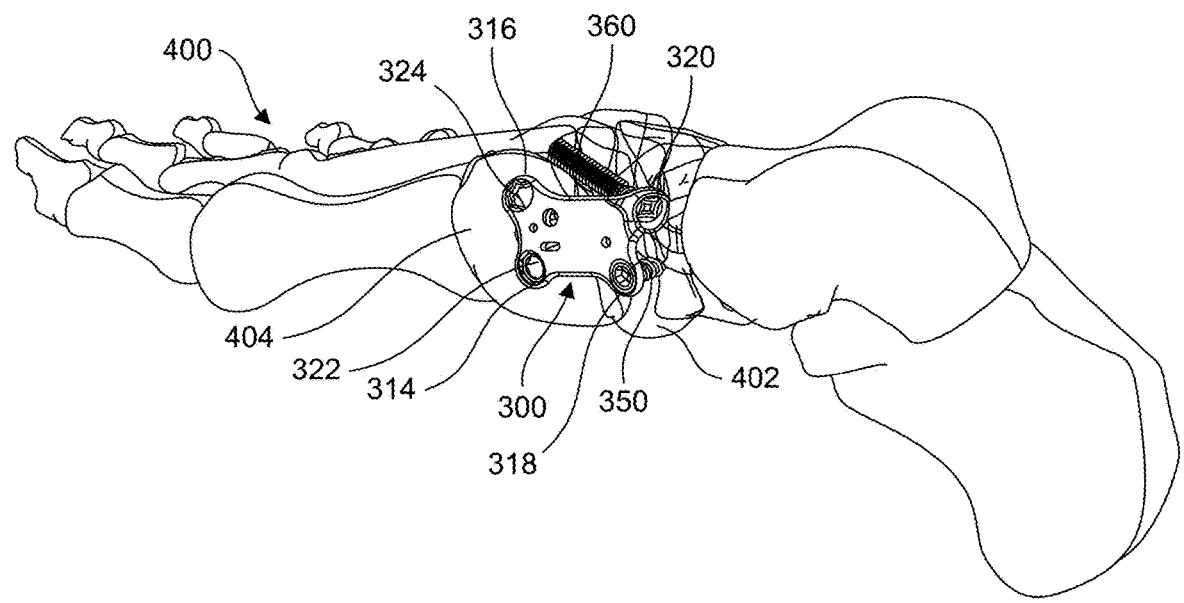
FIG. 37 is a posterior-lateral perspective view of the foot of FIG. 30 with two bone fasteners inserted into the proximal end of the plate, in accordance with an aspect of the present invention.
Figure 38:
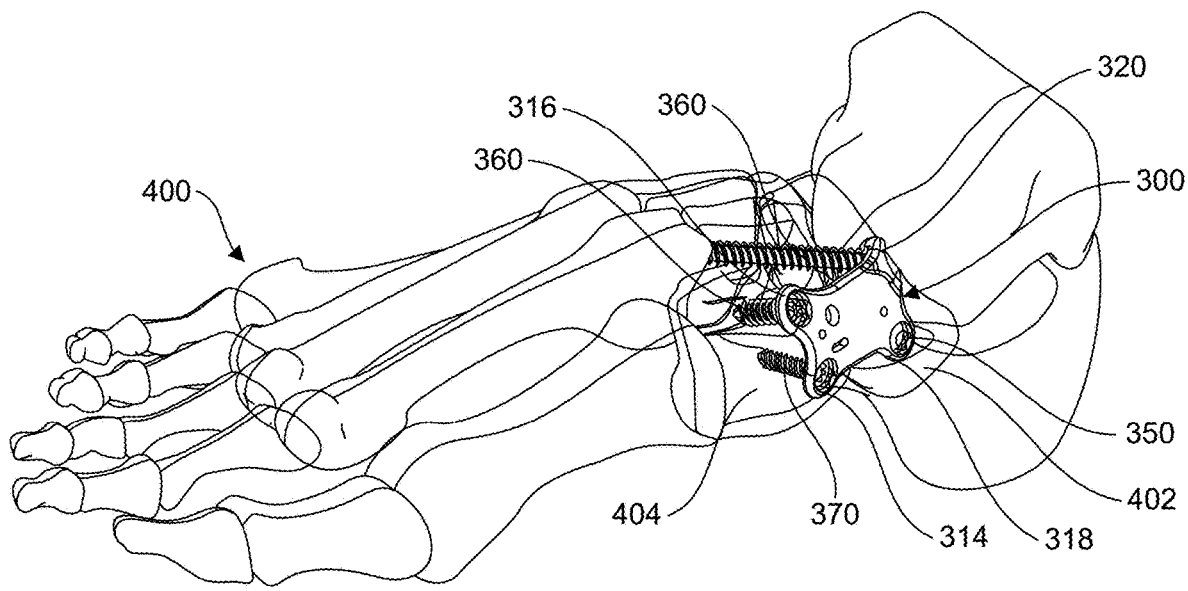
FIG. 38 is a posterior-lateral perspective view of the foot of FIG. 37 with two bone fasteners inserted into the distal end of the plate, in accordance with an aspect of the present invention.

In another embodiment, as shown in FIGS. 34-40, the method may further include using an external compression device (not shown) to compress the navicular-cuneiform joint. Once the joint is compressed, the plantar proximal screw 350 may be inserted into the opening 326 in the first proximal lobe 318, as shown in FIG. 37. The fastener 350 is inserted into the navicular bone 402. Next, the recessed screw or dorsal proximal screw 360 may be inserted into the opening 328 in the second proximal lobe 320, as shown in FIG. 37. The fastener 360 may be inserted through the navicular bone 402 and into the intermediate cuneiform 406. Then, the plantar distal screw 370 may be inserted into the opening 322 in the first distal lobe 314, as shown in FIG. 38. The plantar distal screw 370 may be inserted into the medial cuneiform 404. In addition, with continued reference to FIG. 38, the dorsal distal screw 380 may be inserted into the opening 324 in the second distal lobe 316. The dorsal distal screw 380 may be inserted into the medial cuneiform 404.

Figure 39:
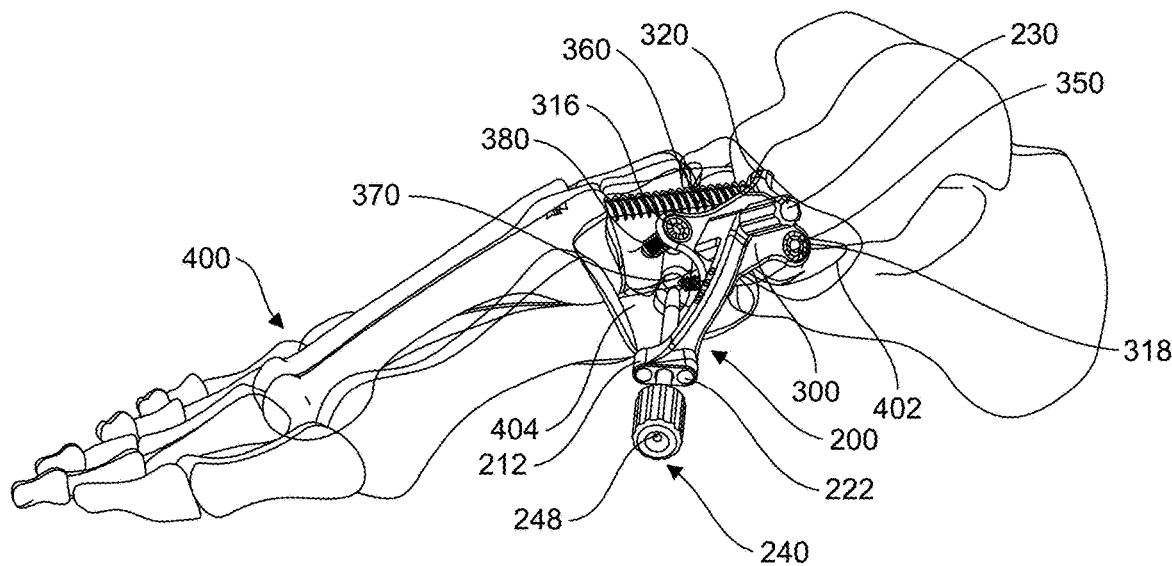
FIG. 39 is a lateral perspective view of the foot of FIG. 38 with the alignment guide apparatus of FIG. 11 coupled to the plate, in accordance with an aspect of the present invention.
Figure 40:
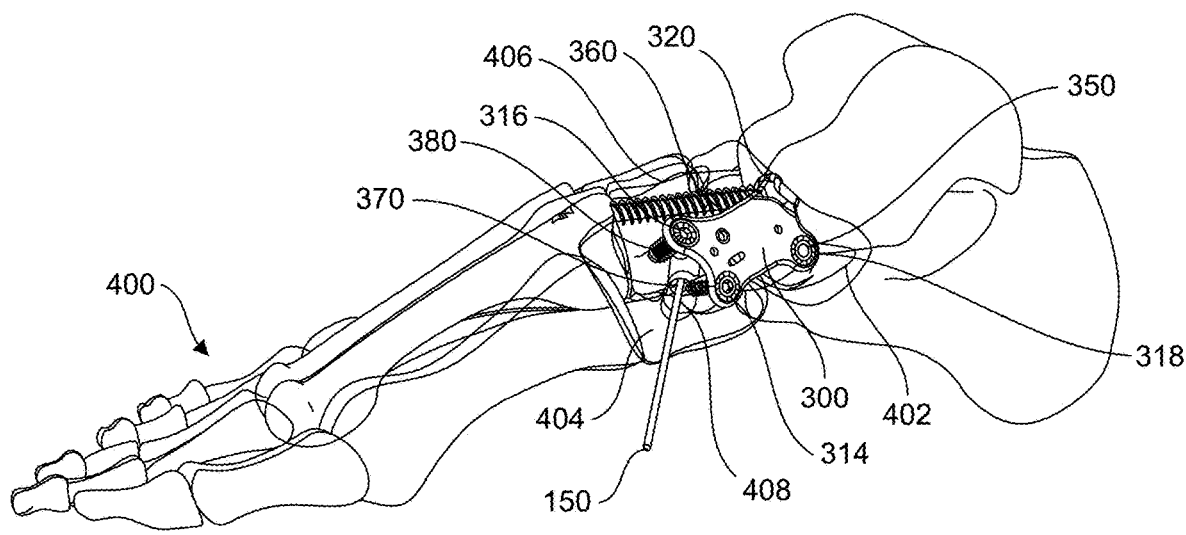
FIG. 40 is an anterior-lateral perspective view of the foot of FIG. 39 with a guide wire inserted into the foot using the alignment guide apparatus and the alignment guide apparatus removed, in accordance with an aspect of the present invention.

Next, as shown in FIG. 39, the alignment guide apparatus 200 may be coupled to the alignment guide openings 342, 344 of the plate 300. The alignment guide apparatus 200 may be coupled to the plate 300 as described in greater detail above, which will not be described again here for brevity sake. After the body 202 is secured to the plate 310, the guide pin protector 240 may be inserted into one of the through holes 222 and positioned to contact the medial cuneiform 404, as shown in FIG. 39. Once the guide pin protector 240 is positioned on the medial cuneiform 404, a k-wire, for example, k-wire 150 may be inserted through the through hole 248 in the tissue protector 240 and into the medial cuneiform 404, as shown in FIG. 40. Next, the tissue protector 240, the fixation member 230 and the body 202 may be removed leaving a k-wire 150 inserted into the medial cuneiform 404. After the alignment guide apparatus 200 is removed, a cannulated drill (not shown) may be obtained and inserted over the k-wire 150 which was inserted using the alignment guide apparatus 200. The drill (not shown) may, for example, be used to create a recessed opening 408 in the medial cuneiform 404, as shown in FIG. 40. The recessed opening 408 may be drilled on a trajectory that does not interfere with any of the inserted bone screws 350, 360, 370, 380. Once the recessed opening 408 is drilled, a fastener 250, for example, a cannulated compression screw, cross-screw, screw or interfrag, may be inserted over the k-wire 150 and through the patient's medial cuneiform 404 and into at least the navicular bone 402, as shown in FIGS. 34-36. The fastener 250 may be, for example, a fully threaded cross-screw. After the fastener 250 is inserted, the k-wire 150 that was inserted with the alignment guide apparatus 200, may be removed, as shown in FIG. 34-36. After all of the fasteners 350, 360, 370, 380 are inserted through the plate 300 and the cross-screw 250 is inserted through the joint, as shown in FIGS. 35, 36 and 45, the procedure may be completed, and the patient's incision may be closed.

Figure 41:
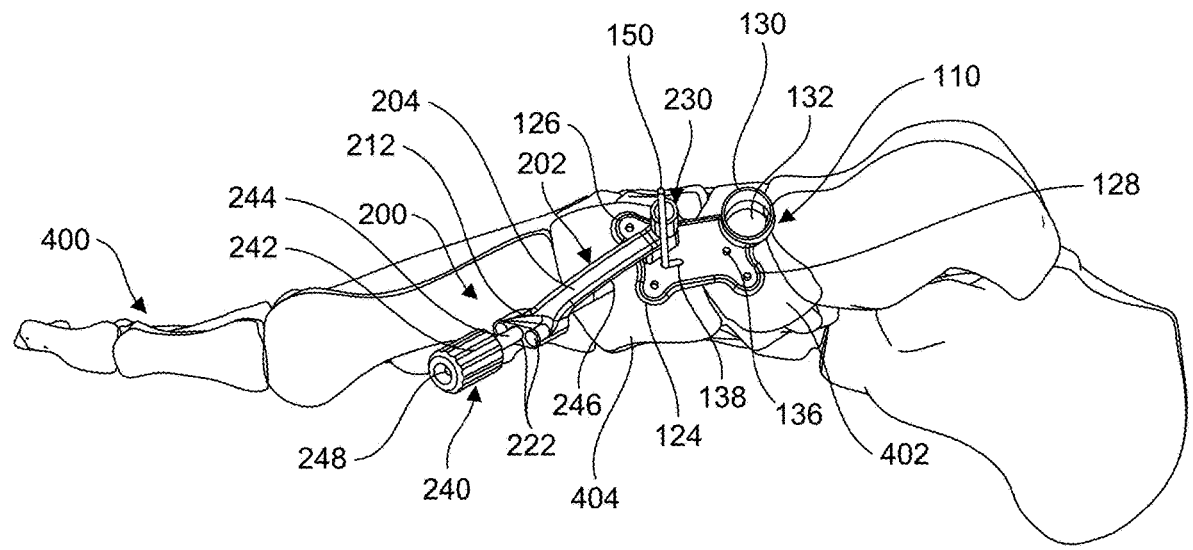
FIG. 41 is a lateral perspective view of the is a side view of the patient's foot of FIG. 27 with the alignment guide apparatus of FIG. 11 coupled to the implant template of FIG. 27, in accordance with an aspect of the present invention.

Referring now to FIGS. 41-44 and with continued reference to FIGS. 27, 28, 34-36 and 45, another alternative embodiment of the method is shown. The alignment guide apparatus 200 may be attached to the template 110 after the template 110 is positioned over the navicular-cuneiform joint with guide wires, k-wires, olive wires or the like. For example, the attachment portion 206 of the alignment guide portion or body 202 may be aligned with the alignment guide openings 140, 142 on the template 110. The alignment protrusion 210 of the attachment portion 206 may be inserted into the first alignment guide opening 140 of the template 110 and the body 202 may be placed in a desired position. Next, the fixation member 230 may be inserted into the through hole 208 in the body 202 and the engagement portion 236 of the fixation member 230 may be coupled to the second alignment guide opening 142 of the template 110. After the body 202 is secured to the template 110, the guide pin protector 240 may be inserted into one of the through holes 222 and positioned to contact the medial cuneiform 404, as shown in FIG. 41.

Figure 42:
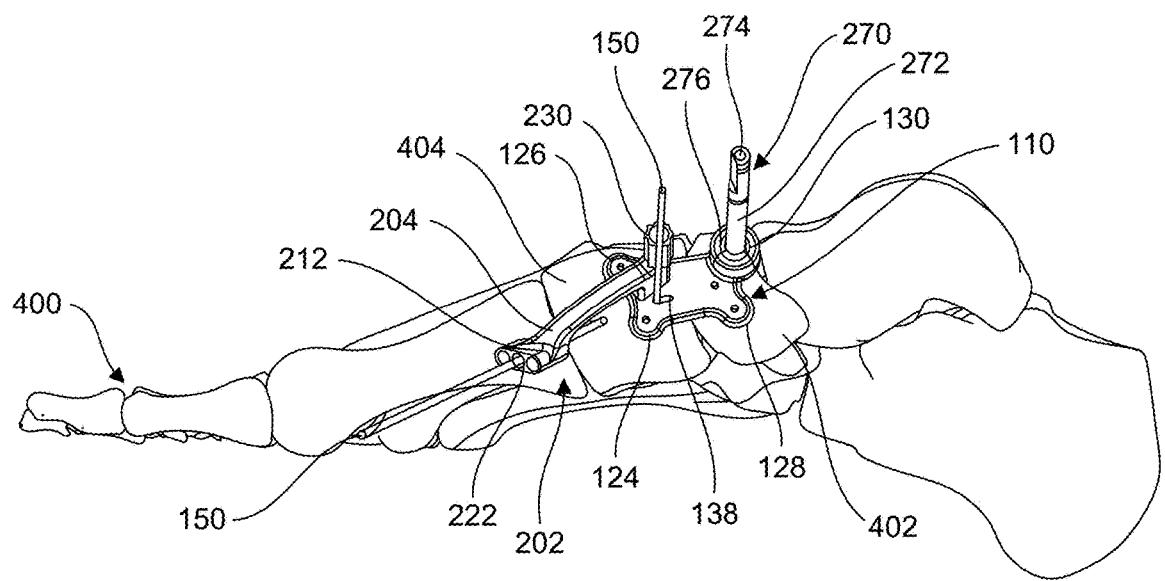
FIG. 42 is a lateral view of the foot of FIG. 41 with a drill bit inserted into the implant template of FIG. 3, in accordance with an aspect of the present invention.
Figure 43:
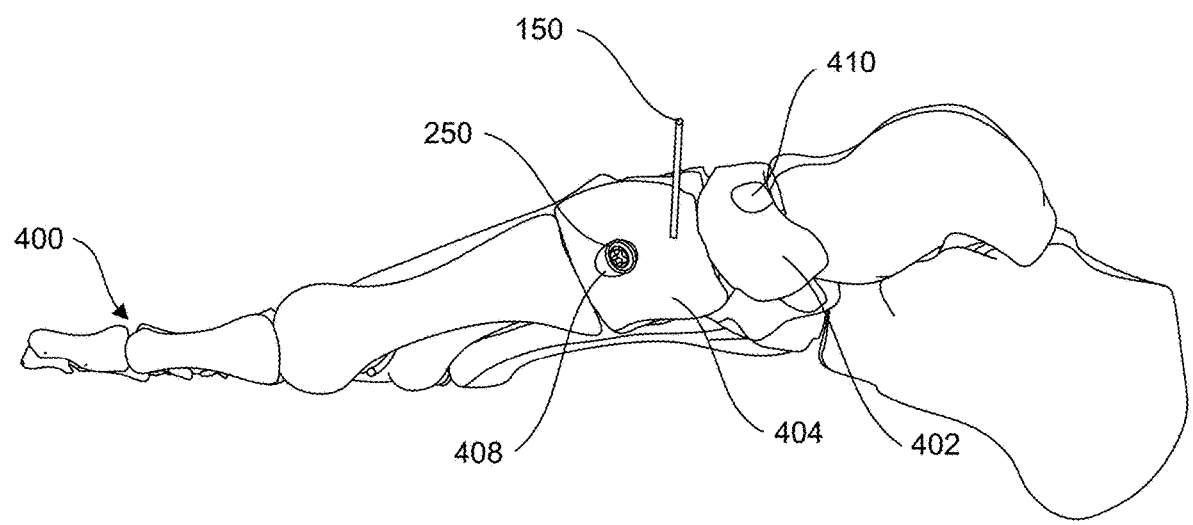
FIG. 43 is a lateral view of the foot of FIG. 42 with the implant template, alignment guide apparatus and drill bit removed from the foot and a compression fastener of the bone fusion system of FIG. 1 inserted into the foot, in accordance with an aspect of the present invention.

After the guide pin protector 240 is positioned on the medial cuneiform 404, a k-wire, for example, k-wire 150 may be inserted through the through hole 248 in the tissue protector 240 and into the medial cuneiform 404, as shown in FIG. 42. Next, the tissue protector 240, the fixation member 230 and the body 202 may be removed leaving the two k-wires 150 inserted into the medial cuneiform 404. After the alignment guide apparatus 200 is removed, a cannulated drill (not shown) may be obtained and inserted over the k-wire 150 which was inserted using the alignment guide apparatus 200. A second drill (not shown) may then be, for example, used to create a recessed or countersunk opening 408 in the medial cuneiform 404, as shown in FIG. 43. Once the recessed opening 408 is drilled, a fastener 250, for example, a cannulated compression screw, may be inserted over the k-wire 150 and through the patient's medial cuneiform 404 and into at least the navicular bone 402. After the fastener 250 is inserted, the k-wire 150 that was inserted with the alignment guide apparatus 200, may be removed, as shown in FIG. 43.

With continued reference to FIGS. 41-43, the template 110 may be used to form a recessed region 410 in the navicular bone 402. The recessed region 410 may be formed by inserting the drill bit 270 into the drill opening 132 in the drill guide member 130, as shown in FIG. 42, and drilling to create a recess in the navicular bone 402. After the recessed region 410 is formed, the olive wire (not shown) may be removed from the alignment opening 136 and the navicular bone 402. Next, the template 110 may be slid off the medial cuneiform 404 and the navicular bone 402 leaving the k-wire 150 which was inserted through the positioning slot 138, as shown in FIG. 43.

Figure 44:
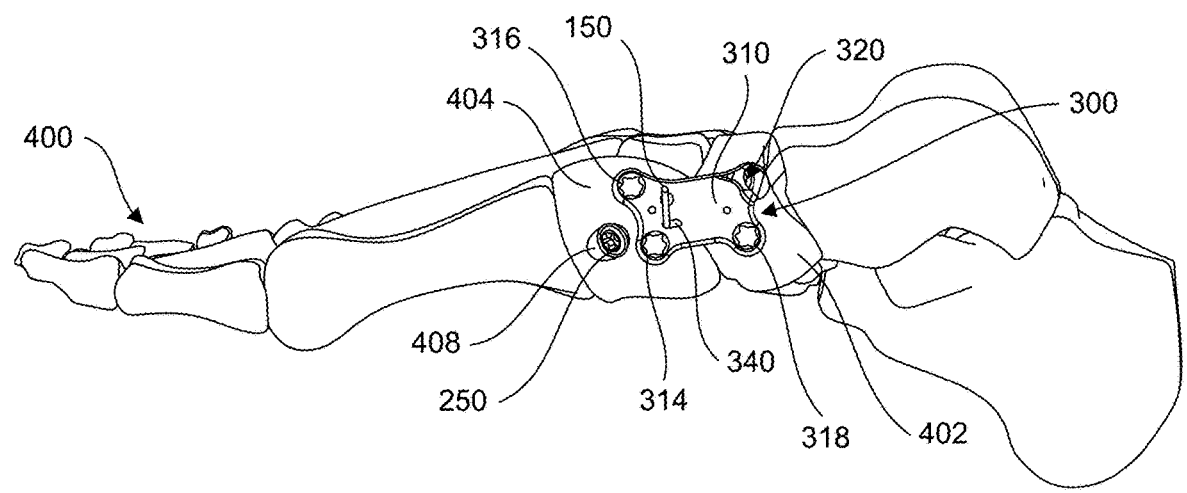
FIG. 44 is a lateral view of the foot of FIG. 43 with the plate of FIG. 19 positioned on the foot, in accordance with an aspect of the present invention.

Once the recessed region 410 is formed and the template 110 removed from the bones 402, 404, the positioning slot 340 of a plate 300 may be inserted over the k-wire 150 and the plate 300 may be slid down the k-wire 150 and aligned on the bones 402, 404, as shown in FIG. 44. The second proximal lobe 320 of the plate 300 may be aligned into the recessed region 410 in the navicular bone 402, as shown in FIG. 44.

Referring now to FIG. 33, a fastener or plantar proximal screw 350 may be inserted into the opening 326 in the first proximal lobe 318 and into the navicular bone 402. Next, a fastener, recessed screw or dorsal proximal screw 360 may be inserted into the opening 328 in the second proximal lobe, angled lobe, or recessed lobe 320. The fastener 360 may be inserted through the navicular bone 402 and into the intermediate cuneiform 406. Then, the plantar distal screw or fastener 370 may be inserted into the opening 322 in the first distal lobe 314, as shown in FIG. 34. The plantar distal screw 370 may be inserted into the medial cuneiform 404. In addition, with continued reference to FIG. 34, the dorsal distal screw or fastener 380 may be inserted into the opening 324 in the second distal lobe 316. The dorsal distal screw 380 may be inserted into the medial cuneiform 404. After all of the fasteners 350, 360, 370, 380 are inserted through the plate 300, the procedure may be completed, and the patient's incision may be closed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A method of using a bone fusion system, comprising:
   making an incision over a navicular-cuneiform joint;
   preparing the joint for fusion;
   coupling an implant template to the joint with at least one wire;
   forming aa recessed region in a navicular bone with the implant template;
   removing the implant template from the navicular-cuneiform joint;
   positioning a plate on the navicular-cuneiform joint;
   and inserting bone screws through the plate to secure the plate to at least two bones of the navicular-cuneiform joint.

2. The method of claim 1, further comprising:
coupling an alignment guide apparatus to the plate.

3. The method of claim 2, wherein the alignment guide apparatus comprises:
a body, the body comprising:
an arm with a first end and a second end;
an attachment portion at the first end; and
an alignment portion at the second end;
a fixation member, wherein the fixation member extends through the attachment portion;
a guide pin protector, wherein the guide pin protector extends through the alignment portion; and
a compression screw configured to engage the guide pin protector.

4. The method of claim 3, wherein the attachment portion comprises a through hole configured to receive the fixation member.

5. The method of claim 3, wherein the alignment portion comprises:
at least one through hole for receiving the guide pin protector.

6. The method of claim 5, wherein the alignment portion is tapered from a first side to a second side.

7. The method of claim 3, wherein the fixation member comprises:
a knob portion; and
a shaft portion extending away from the knob portion.

8. The method of claim 7, wherein the shaft portion comprises:
an engagement region; and
a recessed region positioned adjacent to the engagement region.

9. The method of claim 3, wherein the compression screw has a first end and a second end, the screw further comprising:
a head portion at the first end;
a shaft portion extending away from the head portion to the second end, wherein the shaft portion comprises a smooth region and a threaded region; and
a through hole extending from the first end to the second end.

10. The method of claim 1, wherein the at least two bone screws extend through at least two openings in the plate.

11. The method of claim 1, wherein the implant template comprises:
a first distal lobe positioned on a plantar side of a first end of the implant template;
a second distal lobe positioned on a dorsal side of the first end of the implant template;
a proximal lobe positioned on the plantar side of a second end of the implant template;
an alignment opening positioned near a proximal end of the implant template;
a positioning slot positioned near a distal end of the implant template; and
a proximal drill guide member positioned on the dorsal side of the second end of the implant template.

12. The method of claim 11, wherein the implant template further comprises:
a first alignment guide opening positioned near the distal end of the implant template; and
a second alignment guide opening.

13. The method of claim 1, wherein the plate comprises:
an angled lobe positioned on a dorsal side of a proximal end of the plate, wherein the angled lobe is angled relative to a horizontal plane and a top plane of the plate.

14. The method of claim 13, wherein the angled lobe comprises a bone contacting surface, wherein the bone contacting surface is at least one of a curved or semi-circular shape.

15. The method of claim 14, wherein the plate further comprises:
a first distal lobe positioned on a plantar side of a distal end of the plate;
a second distal lobe positioned on the dorsal side of the distal end of the plate; and
a proximal lobe positioned on a plantar side of the proximal end of the plate.

16. The method of claim 15, wherein each of the lobes comprises an opening extending through the plate from an exterior surface to an interior surface, and wherein the exterior and interior surfaces are non-planar.

17. The method of claim 16, wherein the opening in the proximal lobe comprises a compound angle, wherein the compound angle comprises:
a first angle, wherein the first angle is the angle of a central axis of the opening from a horizontal plane; and
a second angle, wherein the second angle is the angle of the central axis of the opening from a dorsal plane.

18. The method of claim 15, wherein the plate further comprises:
an alignment opening positioned near a proximal end of the plate; and
a positioning slot positioned near the distal end of the plate.

19. The method of claim 15, wherein the plate further comprises:
a first alignment guide opening positioned near the distal end of the plate; and
a second alignment guide opening.

20. A method of using a bone fusion system for fusing bones, comprising:
creating an incision over a navicular-cuneiform joint;
preparing the joint for fusion;
selecting an implant template and a corresponding bone plate that fits the navicular-cuneiform joint, said bone plate comprising a slot;
coupling the implant template to the joint with at least one wire;
forming a recessed region in a navicular bone with the implant template;
removing the implant template from the navicular-cuneiform joint;
positioning the bone plate on the navicular-cuneiform joint and receiving the at least one wire in the slot; and
inserting one or more bone screws through one or more openings in the bone plate to secure the bone plate to at least two bones of the navicular-cuneiform joint.

* * * * *